US012594205B2

(12) United States Patent
Wiggermann

(10) Patent No.: US 12,594,205 B2
(45) Date of Patent: Apr. 7, 2026

(54) DEVICES, SYSTEMS, AND METHODS FOR PROVIDING REMOTE SUPPORT TO A USER OF CARE COMPONENTS

(71) Applicant: Liko Research & Development AB, Luleå (SE)

(72) Inventor: Neal Wiggermann, Batesville, IN (US)

(73) Assignee: Liko Research & Development AB, Luleå (SE)

( * ) Notice: Subject to any disclaimer, the term of this patent is extended or adjusted under 35 U.S.C. 154(b) by 614 days.

(21) Appl. No.: 17/964,358

(22) Filed: Oct. 12, 2022

(65) Prior Publication Data

US 2023/0123333 A1 Apr. 20, 2023

Related U.S. Application Data

(60) Provisional application No. 63/255,720, filed on Oct. 14, 2021.

(51) Int. Cl.
| | |
|---|---|
| *A61G 7/10* | (2006.01) |
| *G16H 40/60* | (2018.01) |
| *G16H 70/20* | (2018.01) |

(52) U.S. Cl.
CPC ......... *A61G 7/1065* (2013.01); *A61G 7/1051* (2013.01); *G16H 40/60* (2018.01); *G16H 70/20* (2018.01)

(58) Field of Classification Search
CPC ........ G16H 40/67; G16H 40/63; G16H 80/00; G16H 40/00; G16H 40/60; G16H 40/40; G16H 40/20
See application file for complete search history.

(56) References Cited

U.S. PATENT DOCUMENTS

| | | |
|---|---|---|
| 6,699,187 B2 | 3/2004 | Webb et al. |
| 9,491,418 B2 | 11/2016 | Iversen et al. |
| (Continued) | | |

FOREIGN PATENT DOCUMENTS

WO 2020/090943 A1 7/2020

OTHER PUBLICATIONS

Welch GF, Sonnenwald DH, Fuchs H, Cairns B, Mayer-Patel K, Soderholm HM, Yang R, State A, Towles H, Ilie A, Ampalam MK, Krishnan S, Noel V, Noland M, Manning JE. 3D medical collaboration technology to enhance emergency healthcare. J Biomed Discov Collab. Apr. 19, 2009;4:4. PMID: 19521951 (Year: 2009).*

*Primary Examiner* — Joseph D Burgess
(74) *Attorney, Agent, or Firm* — Dinsmore & Shohl LLP

(57) ABSTRACT

Assistive control devices, provider assistance systems, systems incorporating the same, and methods for operating the same are disclosed. One system includes an assistive control device and audiovisual communications components communicatively coupled to the assistive control device. The audiovisual communications components are controllable to selectively capture image and audio within the care space and transmit audio. The system further includes subject care components communicatively coupled to the assistive control device. The one or more subject care components are operable locally and remotely. Upon initiation of a remote assistance session, the audiovisual communications components are operated via the assistive control device to move and capture images of a particular area of concern, provide two-way communications between the care space and the assistive control device, and provide indicia. The one or more subject care components are operated remotely and/or locally to complete one or more care tasks.

20 Claims, 10 Drawing Sheets

(56)     References Cited

U.S. PATENT DOCUMENTS

| | | | | |
|---|---|---|---|---|
| 9,576,106 | B2 | 2/2017 | Ahmad | |
| 10,798,339 | B2 | 10/2020 | McMillan et al. | |
| 10,799,318 | B2 | 10/2020 | Sweeney | |
| 10,835,436 | B2 | 11/2020 | Wiggermann | |
| 2011/0214153 | A1* | 9/2011 | Rosenfeld | H04N 7/15 |
| | | | | 725/78 |
| 2014/0139405 | A1* | 5/2014 | Ribble | G16H 40/20 |
| | | | | 345/8 |
| 2014/0272871 | A1* | 9/2014 | Welch | G09B 23/30 |
| | | | | 434/267 |
| 2015/0079565 | A1 | 3/2015 | Miller et al. | |
| 2015/0234998 | A1* | 8/2015 | Slusser | G16H 40/67 |
| | | | | 705/2 |
| 2016/0065909 | A1* | 3/2016 | Derenne | A61B 5/0013 |
| | | | | 348/143 |
| 2016/0300030 | A1 | 10/2016 | Vann, Jr. et al. | |
| 2018/0374577 | A1 | 12/2018 | Bhimavarapu | |
| 2020/0005666 | A1 | 1/2020 | Shen et al. | |
| 2021/0158965 | A1* | 5/2021 | Receveur | G16H 50/20 |

* cited by examiner

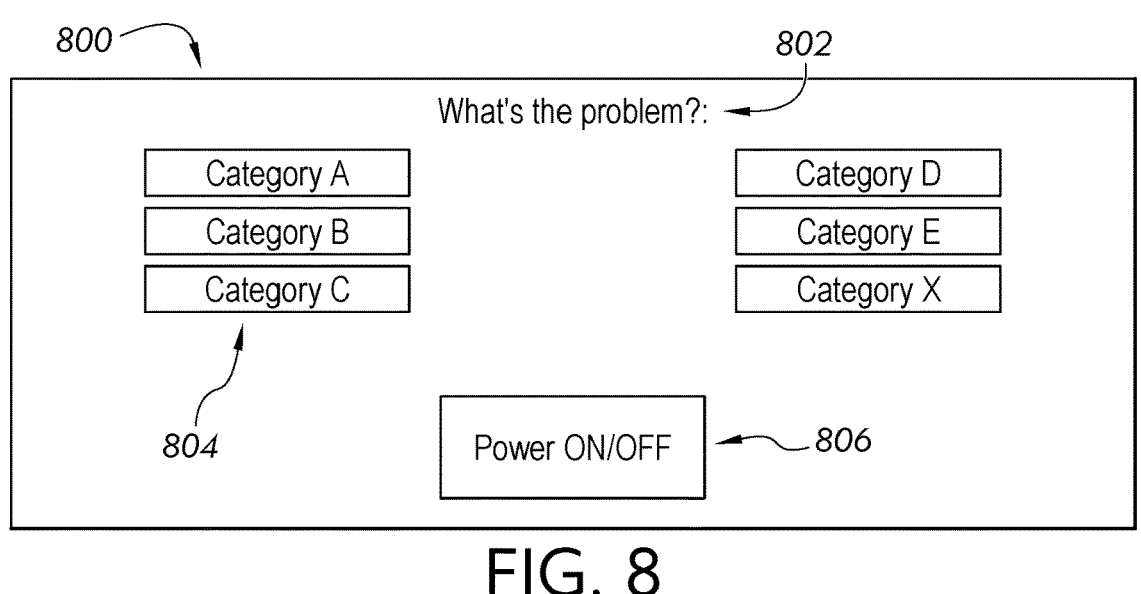
FIG. 8
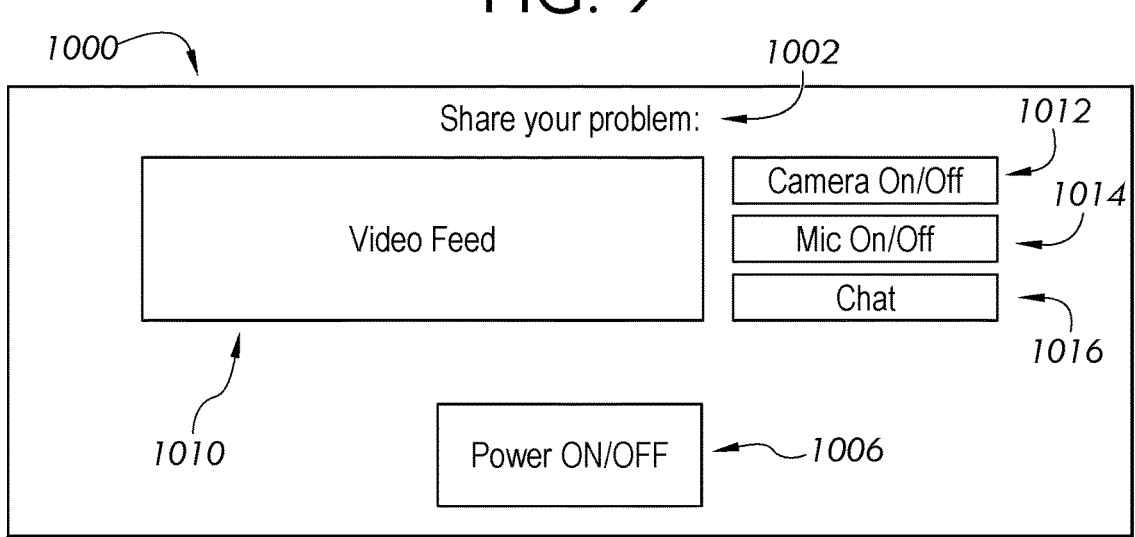
FIG. 9
FIG. 10

DEVICES, SYSTEMS, AND METHODS FOR PROVIDING REMOTE SUPPORT TO A USER OF CARE COMPONENTS

CROSS-REFERENCE TO RELATED APPLICATION

The present application claims the priority benefit of U.S. Provisional Application Ser. No. 63/255,720, filed on Oct. 14, 2021 and entitled "DEVICES, SYSTEMS, AND METHODS FOR PROVIDING REMOTE SUPPORT TO A USER OF CARE COMPONENTS", the entire contents of which is incorporated herein.

BACKGROUND

Field

The present disclosure relates generally to the field of subject care, and more specifically to remote assistance with subject care components.

Technical Background

One illustrative barrier to widespread adoption of safe subject handling and mobility (SPHM) is the need for appropriate training on the use of products and techniques. Without training, caregivers may not use the products or techniques, or may misuse them, which can result in injury, damage to equipment, inefficient practices, and/or the like. Even among facilities with good SPHM programs, unique subject handling situations can challenge well-trained staff. For example, difficulties may be encountered mobilizing a bariatric subject with spine precautions, or moving a double amputee. These situations can occur regularly and specialized knowledge may be helpful in guiding users through these situations to ensure appropriate equipment usage.

SUMMARY

In an aspect, a system includes an assistive control device and audiovisual communications components communicatively coupled to the assistive control device. The audiovisual communications components are controllable via the assistive control device to selectively capture image and audio within at least a portion of the care space and transmit audio to the care space. The system further includes one or more subject care components communicatively coupled to the assistive control device. The one or more subject care components are operable locally and remotely via the assistive control device. Upon initiation of a remote assistance session, the audiovisual communications components are operated via the assistive control device to move and capture images of a particular area of concern within the care space, provide two-way communications between the care space and the assistive control device, and provide indicia within the care space. The one or more subject care components are operated remotely and/or locally to complete one or more care tasks.

In another aspect, assistive control device includes a processor and a non-transitory, processor-readable medium that includes programming instructions thereon. The programming instructions, when executed, cause the processor to establish a communication session with one or more remote audiovisual communications components remotely located in a care space in response to a request for assistance, transmit communications signals to and receive communications signals from the one or more remote audiovisual communications components, cause one or more indicator devices to display indicia within the care space, and direct operation of one or more subject care components within the care space.

In yet another aspect, a provider assistance system includes audiovisual communications components coupled to a remote assistive control device. The audiovisual communications components are controllable via the assistive control device to selectively capture image and audio within at least a portion of the care space and transmit audio to the care space. The provider assistance system further includes one or more subject care components communicatively coupled to the assistive control device. The one or more subject care components are operable locally and remotely via the assistive control device. The provider assistance system further includes one or more indicator devices that include a light emitting component that projects indicia onto at least one of the one or more subject care components and/or a subject. The one or more indicator devices are communicatively coupled to the assistive control device.

In yet another aspect, a method of providing assistance includes receiving, at an assistive control device, a request for assistance, establishing a communication session between the assistive control device and one or more remote audiovisual communications components remotely located from the assistive control device in a care space, transmitting communications signals to and receiving communications signals from the one or more remote audiovisual communications components, causing one or more indicator devices to display indicia within the care space, and directing operation of one or more subject care components within the care space.

Additional features and advantages of the aspects described herein will be set forth in the detailed description which follows, and in part will be readily apparent to those skilled in the art from that description or recognized by practicing the aspects described herein, including the detailed description, which follows, the claims, as well as the appended drawings.

It is to be understood that both the foregoing general description and the following detailed description describe various aspects and are intended to provide an overview or framework for understanding the nature and character of the claimed subject matter. The accompanying drawings are included to provide a further understanding of the various aspects, and are incorporated into and constitute a part of this specification. The drawings illustrate the various aspects described herein, and together with the description serve to explain the principles and operations of the claimed subject matter.

BRIEF DESCRIPTION OF THE DRAWINGS

FIG. 8 schematically depicts an illustrative user interface for connecting to an assistive control device based on specific categories of issues to be solved according to one or more embodiments shown and described herein;

FIG. 9 schematically depicts an illustrative user interface for selecting a solution provided by an assistive control device according to one or more embodiments shown and described herein;

FIG. 10 schematically depicts an illustrative user interface for initiating a communications session with an assistive control device according to one or more embodiments shown or described herein.

DETAILED DESCRIPTION

Figure 1:
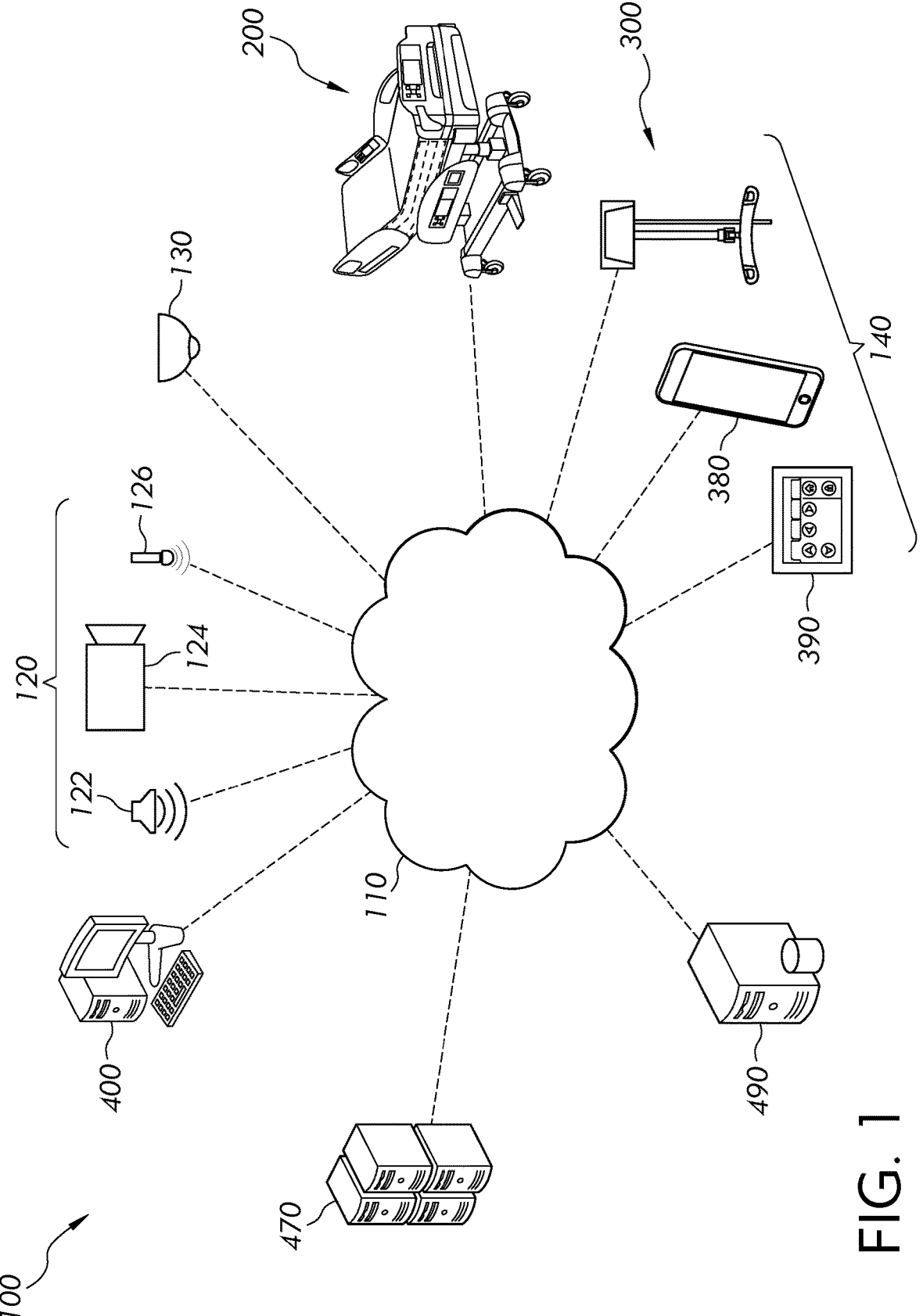
FIG. 1 schematically depicts an illustrative system of networked devices and systems for providing functionality that allows a caretaker to receive instruction and/or assistance for operating one or more subject care components according to one or more embodiments shown and described herein.

Reference will now be made in detail to embodiments of assistive control devices, provider assistance systems, systems that incorporate the assistive control devices and provider assistance system, and methods of operating the same. As depicted in FIG. 1 for example, a system includes a plurality of interconnected devices and systems that provide the functionality described herein. The systems and devices described herein generally provide functionality for allowing a caregiver to use various devices and systems to provide care to a subject and receive remote assistance and/or training that is specific to the devices and systems used and/or according to the subject's particular needs. The remote assistance may be in the form of indicia that show the caregiver how to use equipment, audible instructions, visual instructions, a communications session with a device expert that can interact with the caregiver in real time, remote control of certain devices and systems so that the device expert can show the caregiver what to do or assist the caregiver, and/or the like.

The phrase "communicatively coupled" is used herein to describe the interconnectivity of various components of the system for monitoring the positioning of a subject and means that the components are connected either through wires, optical fibers, or wirelessly such that electrical, optical, and/or electromagnetic signals may be exchanged between the components. It should be understood that other means of connecting the various components of the system not specifically described herein are included without departing from the scope of the present disclosure.

As used herein, the term "positioning" generally refers to how devices, systems, and objects are oriented within a care space, as well as how a subject is oriented on a surface, such as a subject support apparatus or the like. Positioning, as used herein, may generally relate to a positioning of a subject with respect to the surface based on measurements taken from image data relating to the subject's face. However, it should be understood that positioning may be determined from other characteristics of a subject's body. Illustrative examples of a subject's positioning relative to a surface may include a supine positioning (e.g., the subject is laying on a hospital component), a sitting position (e.g., the subject is sitting up on a hospital component or sitting on the edge of a hospital component), a standing position, and/or the like.

While the present disclosure relates generally to care spaces in a clinical setting (e.g., a medical facility such as a hospital (including various wards, rooms, suites, and/or the like thereof), an urgent care facility, a doctor's office, a pharmacy, a mobile care unit, an ambulance, a clinic, a triage center, or the like), it should be appreciated that the devices, systems, and methods described herein may also be implemented in non-clinical settings. For example, the devices, systems, and methods described herein may be implemented in a school environment, a training center environment (e.g., a training center at a hospital, a corporate training center, etc.), and/or the like. Other implementations in non-clinical settings not specifically described herein should generally be understood and are included within the scope of the present disclosure.

Referring now to the drawings, FIG. 1 depicts an illustrative system, generally designated 100, of networked devices and systems for providing functionality that allows a caretaker to receive instruction and/or assistance for operating one or more subject care components according to a particular situation, according to a particular subject, and/or the like. As illustrated in FIG. 1, the system 100 may include at network 110, such as, for example a wide area network (e.g., the internet), a local area network (LAN), a mobile communications network, a public service telephone network (PSTN) and/or other network and may be configured to electronically connect various devices and systems thereto. Nonlimiting examples of systems and devices that may connect via the network 110 to each other include audiovisual communications components 120, an indicator device 130, one or more subject care components 140, an assistive control device 400, a data server 490, and/or one or more machine learning components 470. Such as a subject support apparatus 200, a mobile lift 300, a wall control unit 390, and/or a dedicated device controller 380.

The audiovisual communications components 120 are generally components that provide users of a space in which the audiovisual communications components 120 are located to communicate with the assistive control device 400 and/or a user of the assistive control device 400, as described in greater detail herein. Illustrative examples of audiovisual communications components 120 include, but are not limited to, a speaker 122, a camera 124, and a microphone 126. The speaker 122 is generally any sound emitting device that can be used to broadcast verbal instructions from the assistive control device 400, a user of the assistive control device 400, prerecorded audio instructions stored on the data server 490, and/or the like. The camera 124 is generally any video or still picture imaging device that captures an area in the space in which it is located. In some embodiments, the camera 124 is an omnidirectional camera that has a field of view that allows for capture of images and/or video of a full sphere around the camera 124 or in a circle in a horizontal plane around the camera 124. In other embodiments, the camera 124 may be a camera that has components (e.g., servos or the like) that allow for the camera 124 to be moved (e.g., panned, tilted, or the like) and/or optical components that allow for zooming. In some embodiments, such components may be controllable by the assistive control device 400 such that the assistive control device can ensure that a field of view of the camera 124 includes a particular area of interest. The microphone 126 is generally any sound receiving device that can be used to capture, for example, verbal responses from a caregiver to the assistive control device 400 and/or a user of the assistive control device 400 and/or the like.

While FIG. 1 depicts each of the audiovisual communications components 120 as being separate, the present disclosure is not limited to such. That is, in some embodiments, the audiovisual communications components 120 may be integrated within a single device (e.g., a device that projects audio and records images/sound). For example, an illustrative integrated device may include the camera 124 having a field of view that is capable of capturing images (e.g., pictures and/or an image portion of a video stream) of a particular space, person, or the like. The images may include raw video and/or a 3D depth data stream (e.g., captured by a depth sensor such as a LIDAR sensor or the like). The integrated device may further include the microphone 126 or the like for capturing audio (e.g., an audio portion of a video stream). The integrated device may further include the speaker 122 for emitting audio. In some embodiments, the integrated device may also include a display, which is used for displaying images and/or video to a user. In some embodiments, the integrated device may be any type of computing device (e.g., mobile device, tablet computing device, personal computer, server, etc.). Further, in some embodiments, the camera 124 may be a front facing imaging device (e.g., a camera that faces the same direction as a display of the integrated device) so that a user can view the display and the camera 124 and the microphone 126 can capture video (e.g., audio and images) of the user in real time as the user is viewing the display.

The subject care components 140 are generally devices, systems, and components thereof that may be used to care for a subject. Illustrative examples as used herein include, but are not limited to, a person support apparatus 200, an overhead lift 300, a device controller 380, and/or a wall control unit 390. However, it should be appreciated that other subject care components 140 not specifically described herein are included within the scope of the present disclosure. The person support apparatus 200 may be any apparatus for supporting a subject thereon. Illustrative examples of a person support apparatus 200 include, but are not limited to, a hospital bed, a surgical table, a stretcher, a cot, a gurney, a wheelchair, a chair, a sofa, or the like. Additional details regarding one illustrative person support apparatus 200 will be described herein with respect to FIGS. 2A-2B. The overhead lift 300 is generally a device that includes components for supporting a subject via a sling bar coupled to one or more straps, harnesses, slings, and/or the like. In some embodiments, the overhead lift 300 may be mounted to a rail disposed on a ceiling of a facility and movable along the rail. In other embodiments, the overhead lift 300 may be a mobile lift that is free standing and movable along a floor surface of a hospital or other medical facility. Additional details regarding the overhead lift 300 will be described herein with respect to FIG. 3. The device controller 380 is generally a portable device, such as a personal mobile device (e.g., smartphone, tablet, or the like) that contains software programming thereon for controlling one or more components, such as the person support apparatus 200 and the lift 300. Similarly, the wall control unit 390 may be a device that is communicatively coupled to components for the purposes of controlling the components (e.g., the person support apparatus 200, the lift 300, and/or the like). In some embodiments, the wall control unit 390 may also be used for the purposes of communication and/or remote control of devices, as described in greater detail herein.

The indicator device 130 is generally a device that projects a visual indicator (e.g., indicia or the like) on one or more areas within a space (e.g., on one or more of the subject care components 140, a subject, and/or the like). The indicia projected by the indicator device 130 is not limited by the present disclosure and may be any visual indicator. For example, the indicia may be at least one of an arrow, a diagram, one or more words, and a stop signal. To project a visual indicator, the indicator device 130 may include, for example, a light emitting component or the like that projects the indicia. For example, the indicator device 130 may include a semiconductor laser diode or the like that outputs a beam of coherent light. As used herein, the phrase "semiconductor laser" means any laser device having a semiconductor gain medium that can be pumped electrically or optically to produce a desired wavelength of light. Illustrative gain media include, but are not limited to, GaAs (gallium arsenide), AlGaAs (aluminum gallium arsenide), GaP (gallium phosphide), InGaP (indium gallium phosphide), GaN (gallium nitride), InGaAs (indium gallium arsenide), GaInNAs (indium gallium arsenide nitride), InP (indium phosphide), GaInP (gallium indium phosphide), and/or the like. In some embodiments, the indicator device 130 may be a video projector that projects video onto a surface of a space (e.g., a wall, a projection screen, etc.). In some embodiments, the indicator device 130 may be a combination of a video projector and a laser projector that projects video (e.g., a live video feed) onto a surface and projects indicia over the video to provide augmented reality type indicators to users.

The assistive control device 400 is generally a computing device or the like that includes hardware and software functionality such that remote control and instruction can be completed via the assistive control device 400, as described herein. In some embodiments, the assistive control device 400 may provide a user interface for allowing a user to remotely control components and/or provide instruction as described herein. In some embodiments, the assistive control device 400 may provide a training interface whereby the assistive control device 400 is used to train a user thereon (e.g., such that the user is trained to remotely control components and/or provide instruction as described herein). In other embodiments, the assistive control device 400 may function without user input by automatically providing remote control and/or instruction capabilities as described herein. Additional details regarding the assistive control device 400 will be described herein with respect to FIG. 4.

The data server 490 is generally a device including data storage thereon that can be accessed by any of the components of the system 100 described herein. Illustrative examples of data that may be stored on the data server may include, but are not limited to, stored session data that includes a log of communications and/or remotely controlled movements, data pertaining to a correct mode of operation of a particular component for a particular scenario, image data that is usable for the purposes of determining orientation, pre-recorded instructions for particular learning modules, and/or the like. The hardware within the data server 490 should generally be understood and is not described in further detail herein.

The one or more machine learning components 470 may generally be any machine learning server or collection of machine learning servers that contain a trained machine learning algorithm thereon that, when provided with information from the other components of the system 100 described herein, can automatically determine an appropriate operation of the subject care components 140 for a particular situation and can provide detailed instructions to a care giver and can update instructions as necessary based on caregiver movements, subject movements, and/or the like. That is, the trained machine learning algorithm may act as an alternative or supplemental to a user operating the assistive control device 400, as described herein. The one or more machine learning components 470 are also configured to generate a model from data that is received, the model being usable to assess types of equipment being used, the manner in which equipment is being used, characteristics of the user and a subject, and determine one or more instructions for using, as described in greater detail herein. In some embodiments, the one or more machine learning components 470 may also be particularly trained to receive data from one or more devices (e.g., one or more of the audiovisual communications components 120, one or more of the subject care components 140, the assistive control device, and/or the data server 490), determine from the data that an unsafe activity (or potentially unsafe activity) is occurring and/or whether user expressions, movements, and/or the like are indicative of frustration and/or confusion or any other indicator that assistance could be needed or necessary, and transmit one or more signals to establish an assistance session or prompt a user of the assistive control device 400 to open a connection (e.g., as discussed herein with respect to FIG. 6). For example, image data received by the one or more machine learning components 470 from the camera 124 may include one or more images of a user's face and/or other body parts. The one or more machine learning components 470 may use a trained model specific to facial and/or body recognition to determine that the facial expressions and/or bodily movements are indicative of confusion or frustration, and may automatically transmit a signal to the assistive control device 400 to establish a session as described herein. In another example, the image data received by the one or more machine learning components 470 may be compared with other data, such as, for example, sound data, electronic health record (HER) data, data pertaining to a position of subject care components, data pertaining to forces on subject care components, and/or the like to determine whether the data is indicative of unsafe or potentially unsafe activity. For example, if the received data is indicative of a lift being actuated but the sling loops are not properly connected, or of a bariatric subject is being lifted in a standard sling, a determination may be made that unsafe or potentially unsafe activity is occurring and appropriate action must be taken, as described herein.

Still referring to FIG. 1, the machine learning algorithms utilized by the one or more machine learning components 470 are not limited by the present disclosure, and may generally be any algorithm now known or later developed, particularly those that are specifically adapted for determining and providing instructions or remote control of components, determining unsafe or potentially unsafe activity, determining user confusion, determining user frustration, and/or the like according to embodiments shown and described herein. That is, the machine learning algorithms may be supervised learning algorithms, unsupervised learning algorithms, semi-supervised learning algorithms, and reinforcement learning algorithms. Specific examples of machine learning algorithms may include, but are not limited to, nearest neighbor algorithms, naïve Bayes algorithms, decision tree algorithms, linear regression algorithms, supervised vector machines, neural networks, clustering algorithms, association rule learning algorithms, Q-learning algorithms, temporal difference algorithms, and deep adversarial networks. Other specific examples of machine learning algorithms used by the one or more machine learning components 470 should generally be understood and are included within the scope of the present disclosure. In addition, the hardware within the one or more machine learning components 470 should generally be understood and is not described in further detail herein.

The audiovisual communications components 120 and the subject care components 140 are generally located within a space that is remote from the other components (e.g., the assistive control device 400, the data server 490, and/or the one or more machine learning components 470). For example, the audiovisual communications components 120 and the subject care components 140 may be in a care space such as, for example, a medical facility such as a hospital (including various wards, rooms, suites, and/or the like thereof), an urgent care facility, a doctor's office, a pharmacy, a mobile care unit, an ambulance, a clinic, a triage center, or the like. In contrast, the other components (e.g., the assistive control device 400, the data server 490, and/or the one or more machine learning components 470) are outside the care space in any remote location. The area outside the care space is not limited in the present disclosure and may generally be any location. It should be appreciated that this disparate location of components with respect to each other allows for remote communication and operation of subject care components 140 by an individual that is particularly trained to handle and use particular care components without requiring that individual to be physically present at the care center. For example, a mobility specialist trained by the manufacturer and/or distributor of the subject care components 140 can be located anywhere and still be able to assist users of the subject care components 140 as soon as help is needed so as to avoid or reduce the number of situations where an appropriate care component 140 is not used or incorrectly used.

It should also be appreciated that, in some embodiments, the care space described herein may be a virtually created care space that is used for training purposes, particularly training of users of the assistive control device 400. That is, care space may be a virtually generated space that includes one or more virtual components, virtual people, and/or the like therein that can be particularly configured to move, act in a certain manner, and/or the like. As a result, a person learning how to use the assistive control device 400 may connect to the virtual care space (which may be hosted on the assistive control device 400, on the on the one or more machine learning components 470, the data server 490, or some other device) and interact with the virtual care space in a manner that allows the user of the assistive control device 400 to learn how to appropriately operate the various components of the system 100 via the assistive control device 400, provide appropriate instruction, recognize particular situations, and/or the like.

Figure 2A:
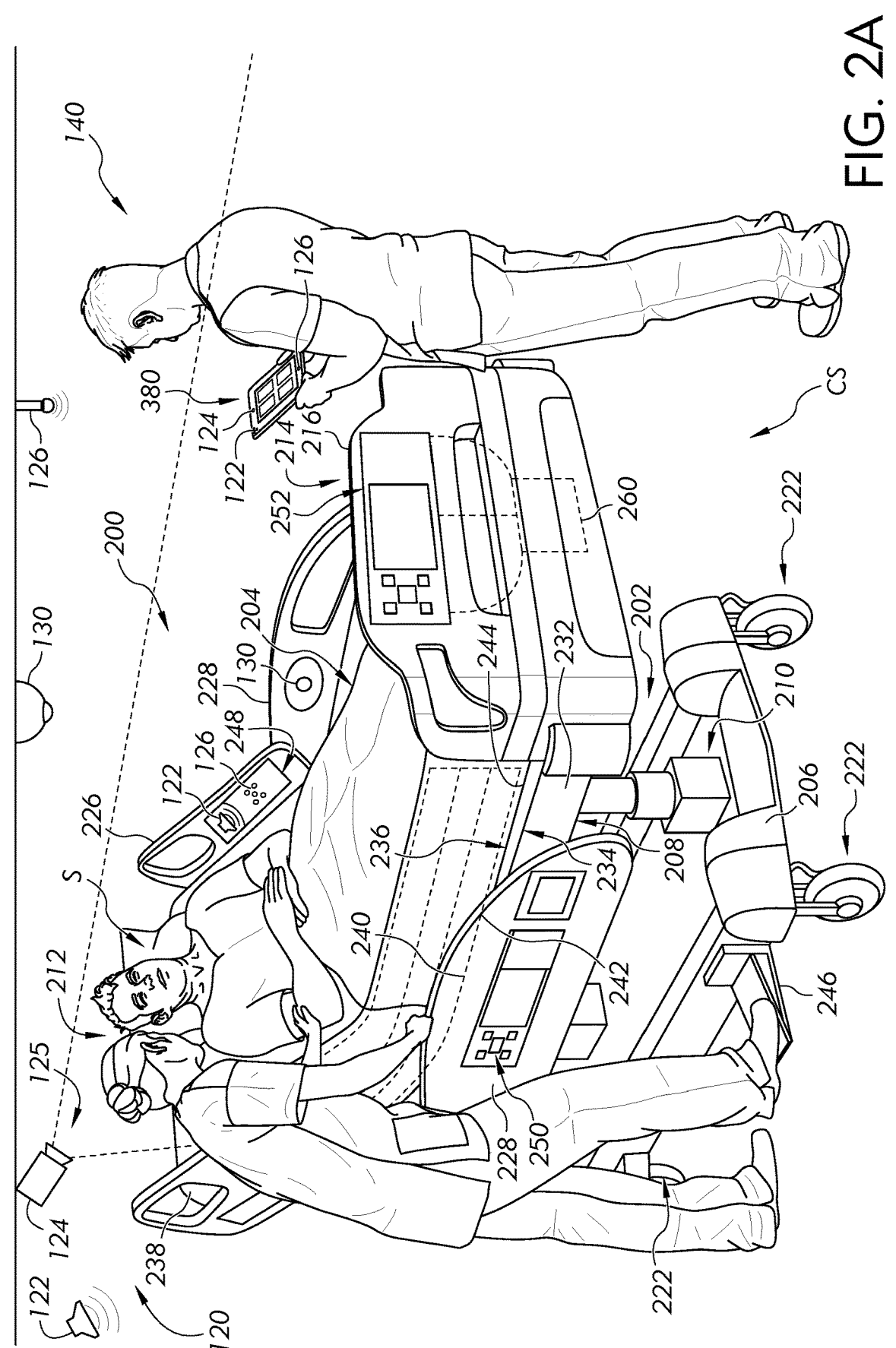
FIG. 2A depicts an illustrative space containing one or more components of the system of FIG. 1 according to one or more embodiments shown and described herein.

FIG. 2A depicts an illustrative space, such as a care space CS according to various aspects. As depicted in FIG. 2A, the care space CS may include, for example, one or more of the audiovisual communications components 120 (e.g., the speaker 122, the camera 124, and/or the microphone 126), the indicator device 130, and/or at least one subject care component 140 (e.g., the person support apparatus 200 and/or the device controller 380 as depicted in FIG. 2A).

The audiovisual communications components 120 are generally disposed in various locations within the care space CS that allow for communication as described herein. For example, one or more cameras 124 (two depicted in FIG. 2A) may be located above the subject care components 140 (e.g., mounted to a ceiling of the care space CS, mounted on an upper portion of a wall, coupled to a floor stand and extended to a height above the subject care components 140, etc.) such that a field of view 125 of each camera 124 includes at least a portion of the subject care components 140 therein. Also depicted in FIG. 2A is a camera 124 integrated within the device controller 380 to allow for two way videoconferencing or the like. In addition, as previously described herein, the cameras 124 may be movable or the like to adjust the field of view 125 so that specific areas within the care space CS can be captured. In another example, one or more speakers 122 may be disposed at various locations within the care space CS. For example, as shown in the embodiment of FIG. 2A, speakers 122 are located near the ceiling of the care space CS, and integrated within the person support apparatus 200 and the device controller 380. However, it should be appreciated that such locations are merely illustrative and other locations are also contemplated. In still another example, one or more microphones 126 may be disposed at various locations within the care space CS. For example, as shown in the embodiment of FIG. 2A, microphones 126 are located near the ceiling of the care space CS, and integrated within the person support apparatus 200 and the device controller 380. However, it should be appreciated that such locations are merely illustrative and other locations are also contemplated.

The indicator device 130 is positioned within the care space CS such that one or more indicia may be projected by the indicator device 130 on a portion of the care space CS, such as, for example, on a subject S, on one or more of the subject care components 140 (e.g., the person support apparatus 200), and/or the like. For example, the indicator device 130 may be positioned on a ceiling of the care space CS, as shown in FIG. 2A. Also shown in FIG. 2A is an indicator device 130 positioned on a portion of the person support apparatus 200. As previously described herein the indicia may be, for example, an arrow, a diagram, one or more words, a stop signal, and/or the like. For example, the indicator device 130 may project an arrow on a portion of the subject S that is to be moved and/or an arrow to show a direction in which the subject S is to be moved. In another example, the indicator device 130 may project a stop sign over the subject S and/or the person support apparatus 200 once a user is to stop moving the subject S. In yet another example, the indicator device 130 may project an outline of a particular positioning of the subject S on the person support apparatus 200 such that a user can move the subject S to correspond to the outline. In still yet another example, the indicator device 130 may project words such as "PLACE LEFT LEG HERE" on the person support apparatus 200 to indicate to a user where the subject's leg should be located. In still yet another example, the indicator device 130 may project a particular indicator that indicates where a user should stand, how a user should manipulate particular components (e.g., which buttons to push), and/or the like. In another example, the indicator device 130 may project an image of the care space onto a wall or other surface (e.g., a live image feed captured via the camera 124) and may superimpose various indicators, diagrams, or the like thereon to provide augmented reality functionality.

As an alternative or an addition to the indicator device 130, a display (not depicted) may be used to display indicia to various individuals within the care space CS in some embodiments. That is, a display, such as a freestanding display, a wall-mounted display, or the like may be communicatively coupled to various components inside the care space CS and/or outside the care space CS (e.g., the assistive control device 400 depicted in FIG. 1) to receive data and information and display indicia corresponding thereto. For example, in some embodiments, the display may display a live feed captured by the camera 124 and/or one or more diagrams, images, superimposed data, and/or the like. In another example, the display may be a tablet with a front-facing camera that displays a real-time camera view with indicia overlaid on the real-time camera view. The overlaid indicia may be based on recognized devices (e.g., subject lift, bed, etc.) determined from a library and/or fiducial markers placed on the devices. The indicia may, for example, indicate how the subject should be positioned, which controls should be used, how sling loops should be attached, and/or the like.

Still referring to FIG. 2A, the various subject care components 140 may be usable to provide care to the subject S. For example, the device controller 380 may include a display 382 (such as a touchscreen display) and internal hardware (not shown) that allows a user of the device controller 380 to adjust one or more settings of components, access information regarding the subject S (e.g., medical records or the like), provide the aforementioned communications capabilities, and/or the like.

In some embodiments, the person support apparatus 200 may be an adjustable support surface having features that allow for adjusting the person support apparatus 200 to conform to particular needs of the subject S. In some embodiments, the person support apparatus 200 may include a standard person support apparatus, an advanced articulation person support apparatus, and/or a chair egress person support apparatus (e.g., available from Hill-Rom Holdings, Inc. (Batesville, IN)). An advanced articulation person support apparatus may support progressive subject mobility stages including a breathe stage (e.g., maintaining optimal head-of-bed (HOB) angle per ventilator-acquired pneumonia (VAP) protocols, avoiding pulmonary complications via continuous lateral rotation therapy (CLRT), and improving respiratory efficiency via percussion and vibration (P&V) therapies, and/or the like), a tilt stage (e.g., maintaining optimal HOB angle per VAP protocols, providing orthostatic conditioning via an 18° reverse Trendelenburg-tilt table, and/or the like), and a sit stage (e.g., facilitating gas exchange via a partial chair position, allowing lung expansion via a chair egress position, preventing subject migration and minimizing repositioning via a stay-in-place system that responds to HOB angle, and/or the like). A chair egress person support apparatus may support progressive subject mobility stages including a stand stage (e.g., building subject strength via a chair egress positions, providing partial weight bearing via a sit-to-stand lift system, and/or the like) and a move stage (e.g., realizing out-of-bed orders via the chair egress positions and/or the sit-to-stand lift system, and/or the like). A standard person support apparatus may or may not support the above-described features and/or may include an add-on (e.g., a "topper" surface to resist or mitigate skin tissue breakdown).

In some embodiments, the person support apparatus 200 includes a frame 202 and a person support surface 204. The frame 202 includes a base 206, an upper frame assembly 208, and a lift system 210 coupling the upper frame assembly 208 to the base 206. The lift system 210 is operable to raise, lower, and tilt the upper frame assembly 208 relative to the base 206. The person support apparatus 200 has a head end 212 and a foot end 214, and further includes a footboard 216 at the foot end 214 of the person support apparatus. While not depicted in FIG. 2A, in some embodiments, a headboard may be located at the head end 212 of the person support apparatus 200. The footboard 216 is coupled to the upper frame assembly 208. The base 206 includes wheels or casters 222 that roll along a floor (not shown) as the person support apparatus 200 is moved from one location to another. A set of foot pedals may be coupled to the base 206 and used to brake and release the wheels or casters 222.

The person support surface 204, may be, for example, an active support surface, a support surface having alternating pressure (AP) features, a support surface having oscillating pressure features, and/or the like. Active person support surfaces are generally powered support surfaces that are configured to alter load distributions with or without an applied load thereon. Support surfaces with AP features provide pressure redistribution via cyclic changes in the loading and unloading (inflation and deflation of air filled cells) as characterized by frequency, duration, amplitude, and/or rate of change parameters. Such AP features may be an effective method to prevent and/or treat pressure injuries. One of the limitations or drawbacks of the AP features is that such AP features may be uncomfortable to certain subjects. That is, when AP features are activated in certain areas of the person support surface, the AP features increase pressure in other support areas of the subject supported by the person support surface. Such an increase in other support areas can be uncomfortable to the subject S supported by the support surface (which may also depend on a size of a bladder, a location of a bladder, a configuration of a bladder, a pressure of a bladder, and/or the like) and/or may cause motion sickness. As such, proper operation (and properly trained users that are appropriately instructed using the systems and methods described herein) can avoid such issues.

As shown in FIG. 2A, the person support apparatus 200 has four siderail assemblies coupled to the upper frame assembly 208 (one is hidden from view). The four siderail assemblies include a pair of head siderail assemblies 226 (sometimes referred to as head rails) and a pair of foot siderail assemblies 228 (sometimes referred to as foot rails). Each of the siderail assemblies 226, 228 is movable between a raised position (e.g., shown on the far end of the person support apparatus 200), and a lowered position (e.g., shown on the near end of the person support apparatus 200). Siderail assemblies 226, 228 are sometimes referred to herein as siderails 226, 228. Each siderail 226, 228 includes a linkage (not shown) coupled to the upper frame assembly 208 and configured to guide the siderails 226, 228 between the raised and lowered positions.

In some embodiments, the upper frame assembly 208 may include a lift frame 232, a weigh frame 234 supported with respect to the lift frame 232, and a person support deck 236. The person support deck 236 is carried by the weigh frame 234 and engages a bottom surface of the person support surface 204. The person support deck 236 includes a head section 238, a seat section 240, a thigh section 242, and a foot section 244, as shown in FIG. 2A. In various embodiments, sections 238, 242, and 244 are each movable relative to the weigh frame 234. For example, the head section 238 may pivotally raise and lower relative to the seat section 240, the foot section 244 may pivotally raise and lower relative to the thigh section 242, and the thigh section 242 may articulate relative to the seat section 240. Additionally, in some embodiments, the foot section 244 may extend and retract to change the overall length of the foot section 244 and, therefore, to change the overall length of the person support deck 236.

In the embodiment depicted in FIG. 2A, the seat section 240 is fixed in position with respect to the weigh frame 234 as the person support deck 236 moves between its various positions including (but not limited to) a horizontal position, a head portion raised (shown in FIG. 2A), and a chair position. In other embodiments, the seat section 240 also moves relative to the weigh frame 234, such as by pivoting and/or translating. In such embodiments, the thigh and foot sections 242, 244 may also translate along with the seat section 240. In the chair position, the head section 238 extends upwardly from the weigh frame 234 and the foot section 244 extends downwardly from the thigh section 242.

In some embodiments, the person support apparatus 200 includes one or more foot pedals 246 coupled to the base 206. In embodiments, the foot pedals 246 may be used to raise and lower portions of the person support apparatus 200. For example, a foot pedal 246 may be used to raise the upper frame assembly 208 relative to the base 206, a foot pedal 246 may be used to lower the upper frame assembly 208 relative to the base 206, a foot pedal 246 may be used to raise the head section 238 relative to the weigh frame 234, and a foot pedal 246 may be used to lower the head section 238 relative to the weigh frame 234. In other embodiments, one or more of the foot pedals 246 may be omitted, or additional foot pedals may be included.

In embodiments, each siderail 226 includes a first user control panel 248 coupled to the inward side of the siderail 226 and each siderail 228 includes a second user control panel 250 coupled to the outward side of the siderail 128. In embodiments, a third user panel 252 coupled to the outward side of the footboard 216. The control panels 248, 250, 252 include various buttons that may be used by a caregiver and/or the subject S to control associated functions of the person support apparatus 200. For example, the first user control panel 248 may include buttons that are used to operate a motor to raise and lower the head section 238, buttons that are used to operate a motor to raise and lower the thigh section 242, and buttons that are used to operate motors to raise, lower, and tilt the upper frame assembly 208 relative to the base 206. The second user control panel 250 may include buttons that are used to operate a motor to raise and lower the foot section 244 and buttons that are used to operate a motor to extend and retract the foot section 244. The third user control panel 252 may include buttons that are used to operate a motor to raise and lower the head section 238, buttons that are used to operate a motor to raise and lower the thigh section 242, buttons that are used to operate motors to raise, lower, and tilt the upper frame assembly 208 relative to the base 206, and buttons that are used to operate a motor to raise and lower the foot section 244 and buttons that are used to operate a motor to extend and retract the foot section 244. Further, the control panels 248, 250, 252 may also incorporate one or more of the speakers 122, the microphones 126, and/or the indicator devices 130 in some embodiments. It should be appreciated that the indicator devices 130 may be used to indicate one or more user interface components on the control panels 248, 250, 252 as a part of instructing a user to operate the person support apparatus 200 as described herein. Alternatively or additionally, in some embodiments, the control panels 248, 250, 252 (or portions thereof) may be selectively illuminated, indicated, and/or the like by the assistive control device 400 (FIG. 1) for the purposes of indicating to a user that a particular interface item should be actuated.

Figure 2B:
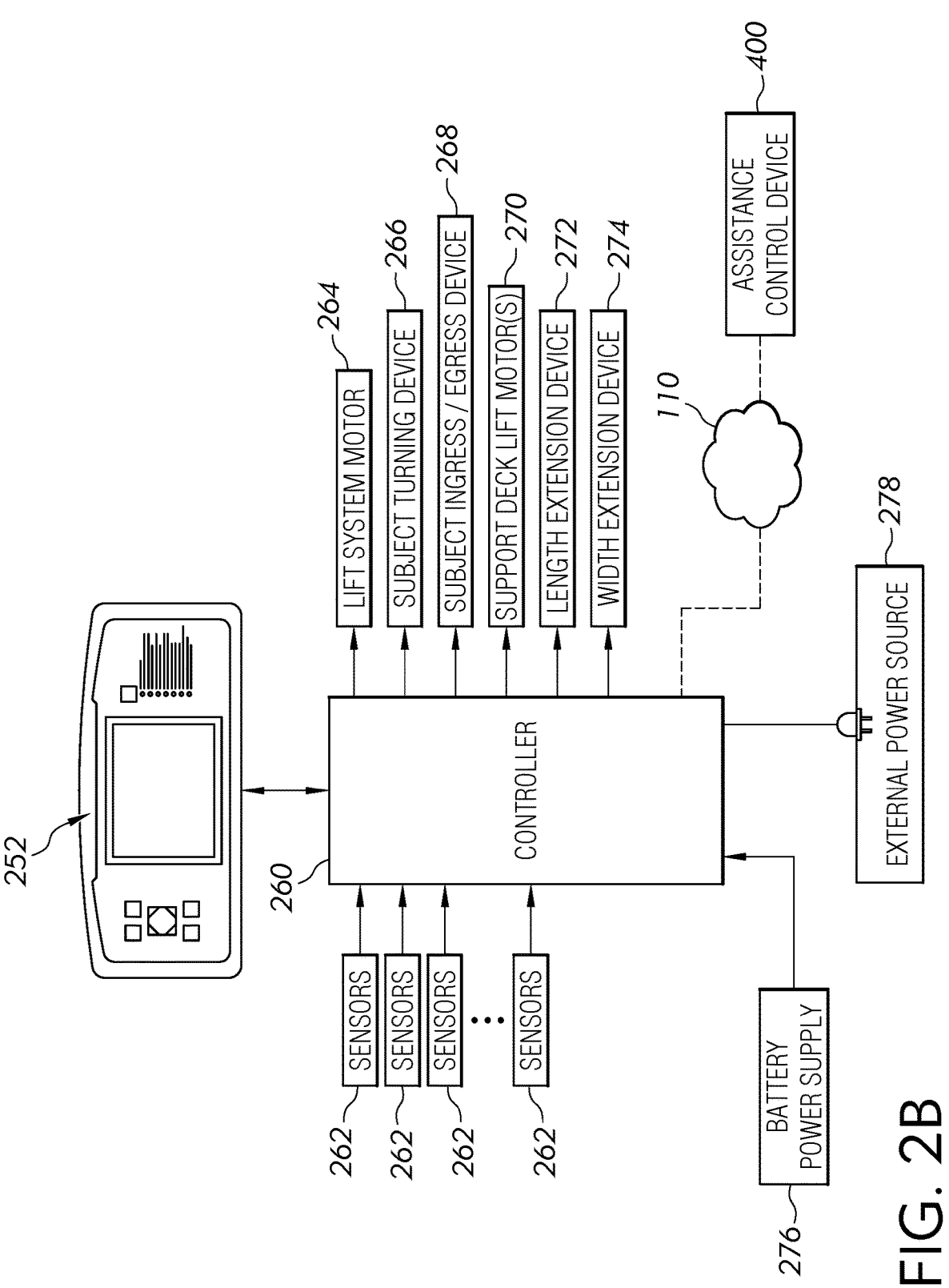
FIG. 2B depicts a block diagram of illustrative components of a person support apparatus according to one or more embodiments shown and described herein.

In various embodiments, one or more components of the person support apparatus 200 are coupled to a controller 260 (e.g., as indicated by the dashed line between the third control panel 252 and the controller 260 in FIG. 2A), which is configured to sense and/or collect information from the components coupled thereto, process the information, and perform one or more actions based on the information. Referring also to FIG. 2B, illustrative components of the person support apparatus 200 that are coupled to the controller 260 include, but are not limited to, one or more sensors 262, a lift motor system 264 that controls raising and lowering of the lift system 210 (FIG. 2A), a subject turning device 266, a subject ingress/egress device 268, one or more support deck lift motors 270 that control raising and lowering of the head section 238, the seat section 240, the thigh section 242, and/or the foot section 244 of the person support deck 236, a length extension device 272 that extends the foot section 244 of the person support deck 236, a width extension device 274 that extends a width of one or more sections of the person support deck 236. In addition, the controller 260 may be communicatively coupled to various other devices described herein via the network 110, such as, for example, the assistive control device 400. As also depicted in FIG. 2B, the controller may also receive electrical power connections from, for example, a battery power supply 276 and/or a external power source 278.

The controller 260 may additionally provide various resources to the person support apparatus 200. Resources include, but are not limited to, providing, for example, processing, storage, software, and information from other systems in the facility to the person support apparatus 200. The components may be coupled wirelessly to the controller 260, such as through a network (not depicted), or the components may be coupled to the controller 260 via wires. Accordingly, in some embodiments, one or more components of the person support apparatus 200 may include wireless communication circuitry, or be communicatively coupled to wireless communication circuitry incorporated into the person support apparatus 200 (not shown).

The controller 260 may be any device having hardware (e.g., chipsets, processors, memory, etc.) for communicatively coupling with the network 100 (FIG. 1). Specifically, the computing device may be a mobile device, a desktop computing device, or a computing device incorporated into or attached to the person support apparatus 200, depending on the particular embodiment. In various embodiments, the controller 260 may be a device accessible by one or more caregivers, such as a computing device located at a nurses' station, in a doctor's office, or carried by the caregiver. In various embodiments, the controller 260 can include an analytics engine. For example, the analytics engine can perform any or all of the functions attributed herein to the controller 260.

In various embodiments, the controller 260 may be a digital safety net (DSN) platform. In such embodiments, the DSN platform may include an analytics engine, a Power over Ethernet (PoE) switch, a router or gateway that receives data from a multitude of sources as described herein and routes risk assessment information to a plurality of output devices such as graphical displays or mobile computing devices assigned to caregivers.

In various embodiments, the controller 260 includes one or more non-transitory memory components, one or more processing devices, a display, a speaker, at least one input device, and network interface hardware. The one or more non-transitory memory components store computer readable and executable instructions that, when executed by the processor, cause the controller 260 to perform one or more functions described herein. In particular, the one or more non-transitory memory components may store computer readable and executable instructions that, when executed by the processor, cause the controller 260 to perform the functions of the various modules described hereinbelow, including but not limited to, analyzing data from one or more components of the person support apparatus 200, calculating a pressure injury score, causing a pressure injury score to be logged in an electronic medical record corresponding to the individual and/or altering a treatment plan for the individual. The at least one input device can include, by way of example and not limitation, a microphone, a keyboard, a touch screen, a mouse, or the like. The network interface hardware may depend on the particular embodiment, and may include the hardware to enable the controller 260 to communicate via the network. The display can include any medium capable of transmitting an optical output such as, for example, a cathode ray tube, light emitting diodes, a liquid crystal display, a plasma display, or the like. Moreover, in some embodiments, the display is a touchscreen that, in addition to providing visual information, detects the presence and location of a tactile input upon a surface of or adjacent to the display. The controller 260 may include additional or fewer components, depending on the particular embodiment. For example, the controller 260 may further include cellular network hardware and a microphone, a mouse, a keyboard, and/or a touch screen.

In various embodiments, the controller 260 is communicatively coupled to one or more input devices of the person support apparatus 200 that collect information indicative of mobility of a person or other factors. For example, referring again to FIG. 2B, in various embodiments, the sensors 262 coupled to the controller 260 may be load cells, an angle sensor, a moisture sensor, or the like, that provide data to the controller 260 which in turn provides the information to the assistive control device 400 for use in determining characteristics of the subject S (FIG. 2A) for the purposes of providing appropriate instruction to a user. Illustrative examples of how the various sensors 262 may be used will be described below.

Referring again to FIGS. 2A-2B, in various embodiments, the person support apparatus 200 includes a number of load cells positioned between the weigh frame 234 and the base 206. Each load cell is configured to produce a voltage or current signal indicative of a weight impressed on that load cell from the weigh frame 234 relative to the base 206. Each of the load cells are weight sensors comprising resistive strain gauges coupled to a deflectable block (not shown), and structurally couple the weigh frame 234 to the base 206. It will be appreciated, however, that other weight detection devices may be used. Such devices may include, but are not limited to, linear variable displacement transducers (LVDTS) and/or other weight detection devices operable in accordance with known capacitive, inductive, or other physical principles. Moreover, alternative person support apparatuses can be employed, including but not limited to, air mattresses or the like. In various embodiments, the load cells generate a signal which is transmitted to the controller

260. In other words, the load cells generate load cell data that is transmitted to the controller 260. As described herein, the controller 260 receives the load cell data and transmits the load cell data accordingly (e.g., to the assistive control device 400 for the purposes of instructing a user how to appropriately position the subject S).

In various embodiments, the person support apparatus 200 further includes an angle sensor coupled to the controller 260. The angle sensor may be, for example, an accelerometer that operates as part of a head of bed angle monitoring system. The angle sensor detects an angle of the head of the bed. In embodiments, the angle sensor is positioned on the back side (e.g., a side opposite the person support surface) of the articulating head section 238 of the person support deck 236 such that the angular position of the angle sensor follows the angular position of the head section 238 through the full range of articulation. However, it is contemplated that the angle sensor may be coupled to another suitable portion of the head section 238, such as, for example, a frame member, a deck panel, a portion of the mattress, or a siderail 226 that moves along with the head section 238. The angle sensor is oriented such that a measurement axis of the angle sensor enables the angle sensor to measure dynamic acceleration along the measurement axis over time. In embodiments, the angle sensor may further measure static acceleration. The static acceleration measurement represents the orientation of the measurement axis of the angle sensor relative to the force of gravity, which is vertical to the true horizon. As the head section 238 is moved from one position to a different position, the measurement axis experiences sufficient changes in gravitational force to resolve the head of bed angle degree changes throughout the range of movement within a specified margin of error. In embodiments, the output generated by the angle sensor is transmitted to the controller 260, which processes the output, including, for example, amplifying the output, and transmitting the output, as described herein (e.g., to the assistive control device 400 for the purposes of instructing a user how to appropriately position the subject S).

Still referring to FIGS. 2A-2B, various embodiments further include at least one moisture sensor coupled to the controller 260. The moisture sensor may be, for example, a moisture sensor that operates as part of a moisture detection system. In embodiments, the moisture sensor detects a moisture level between the subject S supported on the person support surface 204 and the person support surface 204. The moisture sensor may be, by way of example and not limitation, a capacitive sensor, a resistive sensor, or a thermally conductive sensor. It should be appreciated that other types of moisture sensors may be employed. The moisture sensor of various embodiments may be external to the person support apparatus 200, such as a sensor disposed on top of the person support surface 204, or it may be integrated into the person support apparatus 200, such as positioned between a core layer and a ticking of the person support surface 204. Moreover, the moisture sensor may be positioned at any one or more locations along the length and width of the person support apparatus 200. In various embodiments, the moisture sensor is positioned at a seat area of the person support apparatus 200 such that the moisture sensor can detect, for example, incontinence. In some embodiments, the moisture sensor may be coupled to a moisture detection sheet (not shown). The moisture detection sheet may be made of any suitable material, including organic, inorganic, or synthetic materials or fabrics. In some embodiments, fibers of the moisture detection sheet may serve as moisture sensors. In embodiments including a moisture detection sheet, the moisture detection sheet may absorb moisture between the person supported on the person support apparatus 200 and the person support surface and/or redistribute and direct the moisture to the moisture sensor. As described above, the moisture sensor is coupled to the controller 260 and conveys data to the controller 260 in the form of electrical signals indicative of the moisture level between the person supported on the person support apparatus 200 and the person support surface 204. Communication between the moisture sensor and the controller 260 may be wired or wireless. In embodiments, the moisture sensor may transmit raw data regarding the moisture level to the controller 260, while in other embodiments, the moisture sensor may include components to enable the moisture sensor to determine a moisture level and transmit the moisture level to the controller 260. The controller 260 of various embodiments may further transmit the moisture level to external components as described herein for the purposes of providing instruction (e.g., to the assistive control device 400 for the purposes of instructing a user how to appropriately move the subject S to remove soiled linens or the like).

Figure 3:
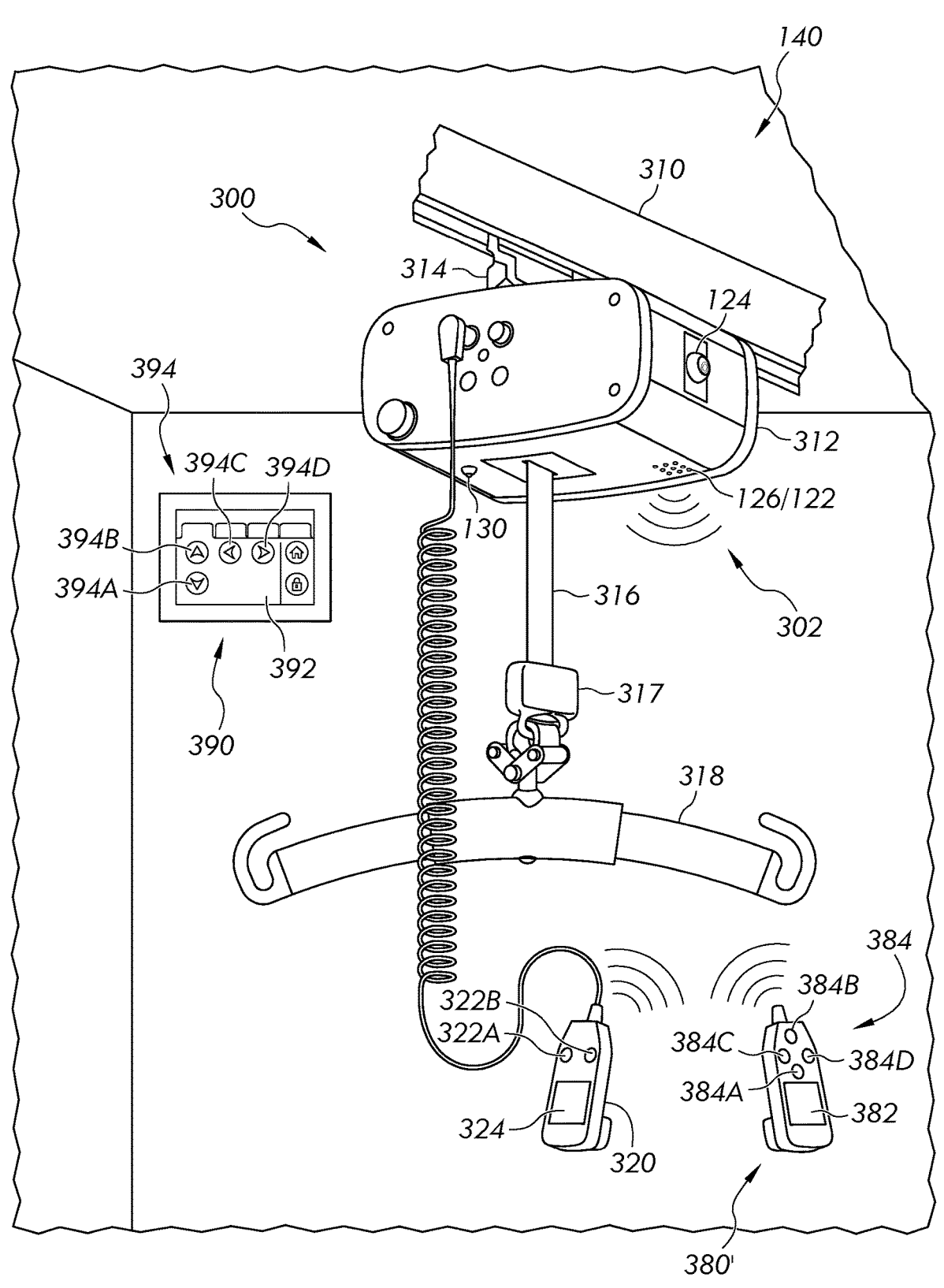
FIG. 3 schematically depicts illustrative subject care components according to one or more embodiments shown and described herein.

Referring now to FIG. 3, other illustrative subject care components 140 are depicted. More specifically, FIG. 3 depicts an illustrative overhead lift 300, a wall control unit 390, and another illustrative dedicated device controller 380'. As will be discussed in greater detail below, each of the components of the subject care components 140 depicted in FIG. 3 may be usable by a user according to instructions that are provided to ensure correct usage.

The rail-mounted lift 300 generally includes an assembly 302 coupled to a rail 310. More specifically, the assembly 302 includes a lift unit 312 that is slidably coupled to the rail 310 via a carriage 314. The lift unit 312 may be used to support and/or lift a subject with a lifting strap 316 which is coupled to a motor (not shown) contained within the lift unit 312. The motor facilitates extending or retracting the lifting strap 316 from the lift unit 312, thereby raising and lowering a subject attached to the lifting strap 316.

In the embodiment of the rail-mounted lift 300 depicted in FIG. 3, a subject may be attached to the lifting strap 316 with a sling bar 318 or a similar accessory attached to the lifting strap 316 via a connection piece 317. More specifically, the sling bar 318 or a similar accessory may be attached to a harness or sling in which the subject is positioned, thereby facilitating the lifting operation.

Various components of the assembly 302, such as the lift unit 312 and/or components thereof, may be operated with a hand control unit 320 that is communicatively coupled to the lift unit 312, the wall control unit 390, and/or the dedicated device controller 380'. In the embodiment shown in FIG. 3, the hand control unit 320 is tethered (e.g., directly wired) to the lift unit 312. In other embodiments, the hand control unit 320 may be omitted. Rather, control of the lift unit 312 is completed via one or more of the wall control unit 390 and the dedicated device controller 380'.

In some embodiments, the hand control unit 320 may include a display 324 and/or one or more user interface controls 322A, 322B. The display 324 is generally any liquid crystal display (LCD), light emitting diode (LED) display, electronic ink (e-ink) display, or the like that can display information to a user. In some embodiments, the display 324 may be configured as an interactive display that can receive user inputs (e.g., a touch screen display or the like). The one or more user interface controls 322A, 322B may be hardware components that receive inputs from a user and transmit signals corresponding to the inputs, such as a keyboard, a mouse, a joystick, a touch screen, a remote control, a pointing device, a video input device, an audio input device, a haptic feedback device, and/or the like. In some embodiments, the display 324 and one or more of the user interface controls 322A, 322B may be combined into a single device, such as a touchscreen display or the like. The display 324 and/or the one or more user interface controls 322A, 322B may be used, for example, to allow a user to manually input information pertaining to an identity of the user, an identity of a subject, a location or sub-location of the assembly 302, to provide instructions for programming and/or pairing the assembly 302 with one or more other components, and/or the like. In some embodiments, the display 324 and/or the one or more user interface controls 322A, 322B may be selectively illuminated, indicated, and/or the like by the assistive control device 400 (FIG. 1) for the purposes of indicating to a user that a particular interface item should be actuated.

Still referring to FIG. 3, the wall control unit 390 can provide connectivity, location, status, configuration, and (unloaded) control; connect to the rail-mounted lift 300 via a wireless (e.g., Bluetooth) connection, connect to the dedicated device controller 380', connect to a remote display, and/or connect to the assistive control device 400 (FIG. 1) via a wired and/or a wireless (e.g., Wi-Fi) connection. In some embodiments, the wall control unit 390 can be powered by a wall plug or be hardwired into an existing electrical system. In some embodiments, the wall control unit 390 can be battery powered such that the wall control unit 390 is removable from a wall plug or hardwired electrical system and still operable. In some embodiments, the various components can be integrated with clinical data to track lifts per subject over time and/or integrated with service data for the purposes of providing device status, software management, and/or the like, as discussed in greater detail herein. In addition, the wall control unit 390 can be integrated with clinical data to track lifts per subject over time and/or integrated with service data for the purposes of providing device status, software management, and/or the like.

The wall control unit 390 includes one or more components that provide functionality for using the lift unit 312. For example, the wall control unit 390 may cause the motor within the lift unit 312 to extend or retract the lifting strap 316, move components up/down, move components laterally, activate the lift unit 312, pair a subject with a lift unit 312, return a lift unit 312 to a "home" position/location, receive information from a lift unit 312 (e.g., battery status, weight of load supported by lift unit 312, movement history, associated subjects, etc.), perform an emergency stop of the lift unit 312, reset the lift unit 312, and/or the like. In another example, the wall-mounted control includes components for using the person support apparatus 200 (FIG. 2A) and/or any other subject care component 140.

Still referring to FIG. 3, the wall control unit 390 may include, for example, a display 392 and/or one or more user interface controls 394A, 394B, 394C, 394D (collectively, 394). The display 392 is generally any liquid crystal display (LCD), light emitting diode (LED) display, electronic ink (e-ink) display, or the like that can display information to a user. In some embodiments, the display 392 may be configured as an interactive display that can receive user inputs (e.g., a touch screen display or the like). The one or more user interface controls 394 may be hardware components that receive inputs from a user and transmit signals corresponding to the inputs. The embodiment of FIG. 3 includes user interface controls 394 in the form of a touch screen. However, other user interface controls are contemplated and included within the scope of the present disclosure, including, but not limited to, a keyboard, a mouse, a joystick, a remote control, a pointing device, a video input device, an audio input device, a haptic feedback device, and/or the like. The display 392 and/or the one or more user interface controls 394 may be used, for example, to allow a user to interact with the wall control unit 390 for the purposes of moving components up/down, moving components laterally, activating the lift unit 312, pairing a subject with a lift unit 312, returning a lift unit 312 to a "home" position/location, receiving information from a lift unit 312 (e.g., battery status, weight of load supported by lift unit 312, movement history, associated subjects, etc.), performing an emergency stop of the lift unit 312, resetting the lift unit 312, and/or the like. In some embodiments, the display 392 and/or the one or more user interface controls 394 may be selectively illuminated, indicated, and/or the like by the assistive control device 400 (FIG. 1) for the purposes of indicating to a user that a particular interface item should be actuated.

Still referring to FIG. 3, the dedicated device controller 380' includes one or more components that provide functionality for using the lift unit 312. For example, the dedicated device controller 380' may include one or more components for causing the motor within the lift unit 312 to extend or retract the lifting strap 316, moving components up/down, moving components laterally, activating the lift unit 312, pairing a subject with a lift unit 312, returning a lift unit 312 to a "home" position/location, receiving information from a lift unit 312 (e.g., battery status, weight of load supported by a lift, movement history, associated subjects, etc.), performing an emergency stop of the lift unit 312, resetting the lift unit 312, and/or the like. In another example, the dedicated device controller 380' includes components for using the person support apparatus 200 (FIG. 2A) and/or any other subject care component 140.

Still referring to FIG. 3, the dedicated device controller 380' may include, for example, a display 382 and/or one or more user interface controls 384A, 384B, 384C, 384D (collectively, 384). The display 382 is generally any liquid crystal display (LCD), light emitting diode (LED) display, electronic ink (e-ink) display, or the like that can display information to a user. In some embodiments, the display 382 may be configured as an interactive display that can receive user inputs (e.g., a touch screen display or the like). The one or more user interface controls 384 may be hardware components that receive inputs from a user and transmit signals corresponding to the inputs. The embodiments of FIG. 3 include user interface controls 384 in the form of physical buttons. However, other user interface controls are contemplated and included within the scope of the present disclosure, including, but not limited to, a keyboard, a mouse, a joystick, a remote control, a pointing device, a video input device, an audio input device, a haptic feedback device, a touch screen, and/or the like. In some embodiments, the display 382 and one or more of the user interface controls 384 may be combined into a single device, such as a touchscreen display or the like. The display 382 and/or the one or more user interface controls 384 may be used, for example, to allow a user to interact with the dedicated device controller 380' for the purposes of moving components up/down, moving components laterally, activating the lift unit 312, pairing a subject with a lift unit 312, returning a lift unit 312 to a "home" position/location, receiving information from a lift unit 312 (e.g., battery status, weight of load supported by lift unit 312, movement history, associated subjects, etc.), performing an emergency stop of the lift unit 312, resetting the lift unit 312, and/or the like. In some embodiments, the display 382 and/or the one or more user interface controls 384 may be selectively illuminated, indicated, and/or the like by the assistive control device 400 (FIG. 1) for the purposes of indicating to a user that a particular interface item should be actuated.

Still referring to FIG. 3, in some embodiments, the dedicated device controller 380' may be a portable electronic device, such as a smartphone, a tablet computing device, a laptop, and/or the like. In such embodiments, the dedicated device controller 380' may contain software programming thereon (e.g., an app or the like) that generates an electronic user interface when the software programming is executed. Further, the software programming, when executed, can cause the dedicated device controller 380' to complete one or more tasks upon receiving particular inputs from a user via the user interface controls 384. However, it should be understood that the dedicated device controller 380' can also be used for other purposes other than those described herein, as is typical for portable electronic devices (e.g., making telephone calls, sending text messages, sending emails, browsing the internet, and/or the like).

In some embodiments, the dedicated device controller 380' may be a standalone unit that is particularly used for the purposes described herein. That is, the dedicated device controller 380' may solely be used for the purposes of displaying information pertaining to a particular subject, providing a user input that is usable to control various components, such as the lift unit 312, and/or the like. As such, the dedicated device controller 380' may only have software programming that is suitable for the purposes described herein, and may lack programming for executing other processes.

As described herein, one or more of the subject care components 140 may, in some embodiments, include one or more of the audiovisual communications components 120 and/or the indicator device 130 integrated therein. For example, as depicted in FIG. 3, the lift unit 312 may include, for example, the microphone 126 and/or the speaker 122, the camera 124, and/or the indicator device 130 integrated within the body thereof. While not specifically depicted in FIG. 3, the dedicated device controller 380' and/or the wall control unit 390 may also incorporate one or more subject care components 140 and/or the indicator device 130 as well.

Figure 4A:
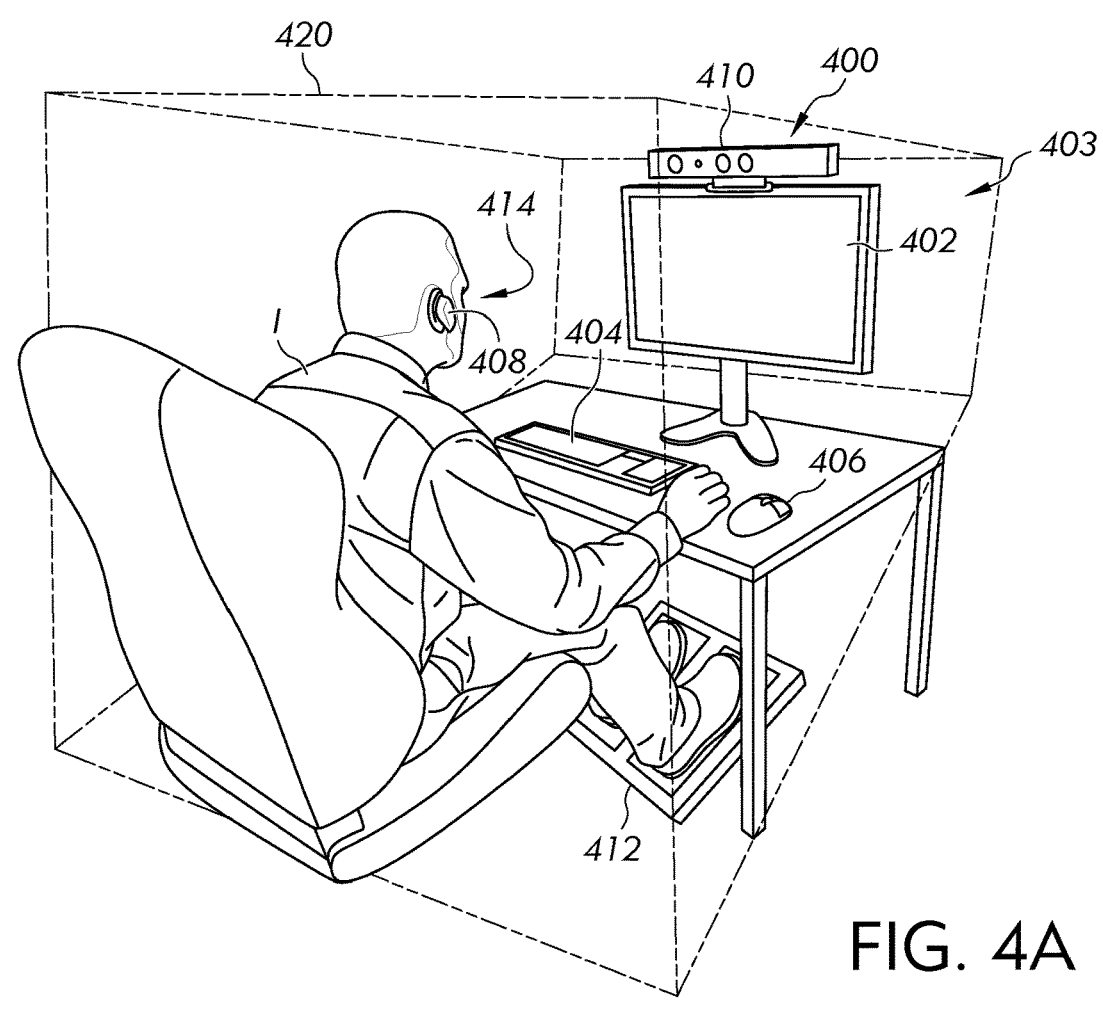
FIG. 4A schematically depicts an illustrative assistive control device according to one or more embodiments shown and described herein.
Figure 4B:
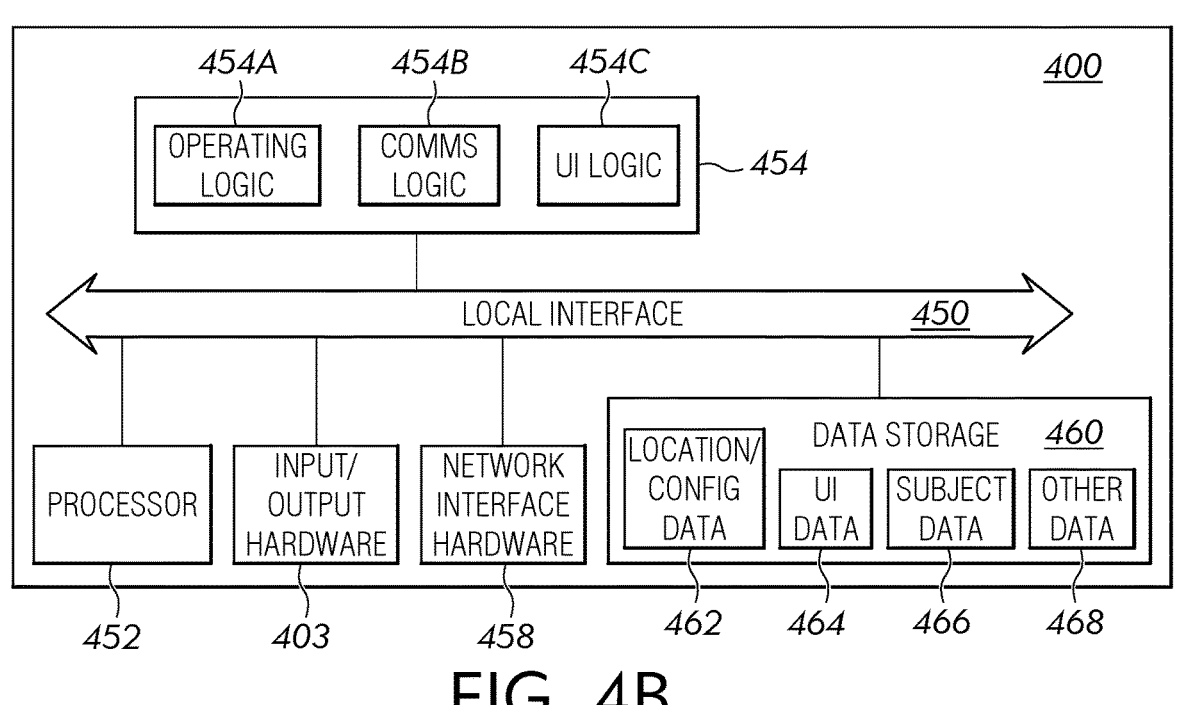
FIG. 4B depicts a block diagram of illustrative internal components of the assistive control device of FIG. 4A according to one or more embodiments shown and described herein.

FIGS. 4A-4B depict one illustrative embodiment of the assistive control device 400. As depicted in the embodiment FIG. 4A, the assistive control device 400 provides an interface for an instructor I (e.g., a specialist, a trainer, a consultant, or the like) to interact with one or more users within the care space CS (FIG. 2A) for the purposes of providing remote instruction, advice, suggestions, remotely controlling components, and/or the like. However, as previously described herein, in other embodiments, the assistive control device 400 may utilize automated processes and/or incorporate machine learning for the purposes of providing remote instruction, advice, suggestions, remotely controlling components, and/or the like. In such embodiments, the various interaction components described with respect to FIG. 4A may be optional or omitted.

As depicted in FIG. 4A, the assistive control device 400 may be configured as a workstation or the like that includes various components such as (but not limited to) a display 402, one or more input/output hardware 403 such as a keyboard 404, a mouse 406, an audio communications piece 408, an imaging device 410, and/or a foot controller 412. In some embodiments, the assistive control device 400 may further include a face worn display 414. The instructor I may use the various input devices for interacting with users in some embodiments. For example, the instructor I may transmit and/or receive audio communications via the audio communications piece 408 (e.g., an earpiece having a speaker and a microphone). In another example, the instructor may be provided with videoconference capabilities via the display 402 and/or the imaging device 410. The imaging device 410 may capture a scene 420 including the instructor I and transmit the scene 420 to a remote component (e.g., a display) such that persons viewing the remote component can see the instructor's gestures or the like.

The various internal components that control operation of the components depicted in FIG. 4A are shown in FIG. 4B. More specifically, as depicted in FIG. 4B, the assistive control device 400 may further include a local interface that communicatively interconnects the various components, including, but not limited to, a processor 452, a non-transitory memory component 454, the input/output hardware 403, network interface hardware 458, and/or a data storage component 460.

The non-transitory memory component 454 may be configured as a volatile and/or a nonvolatile computer-readable medium and, as such, may include random access memory (including SRAM, DRAM, and/or other types of random access memory), flash memory, registers, compact discs (CD), digital versatile discs (DVD), and/or other types of storage components. As such, the non-transitory memory component 454 may be referred to as a non-transitory, processor-readable storage medium. Additionally, the non-transitory memory component 454 may be configured to store various processing logic, such as, for example, operating logic 454A, communications logic 454B, and/or user interface (UI) logic 454C (each of which may be embodied as a computer program, firmware, or hardware, as an example). A local interface 450 is also included in FIG. 4B and may be implemented as a bus or other interface to facilitate communication among the components of the assistive control device 400.

The processor 452 may include any processing component configured to receive and execute instructions (such as from the data storage component 460 and/or the non-transitory memory component 454). The input/output hardware 403 may include any of the components depicted in FIG. 4A and/or other components not depicted for receiving, sending, and/or presenting data (e.g., a device that allows for direct or indirect user interaction with the various components described herein via the assistive control device 400). The network interface hardware 458 may include any wired or wireless networking hardware, such as a modem, LAN port, wireless fidelity (Wi-Fi) card, WiMax card, mobile communications hardware, and/or other hardware for communicating with other networks and/or devices.

It should be understood that the data storage component 460 may reside local to and/or remote from the assistive control device 400 and may be configured to store one or more pieces of data and selectively provide access to the one or more pieces of data. As illustrated in FIG. 4B, the data storage component 460 may store location and configuration data 462, user interface data 464, subject data 466, and/or other data 468. The location and configuration data 462 may generally be data pertaining to a location and/or a configuration of components that are used by a user and may be the subject of instruction as described herein. Such data may include images of components that show relative positioning, data from various sensors disposed within the components, data pertaining to a state of certain components, data relating to a history of component use, and/or the like. In some embodiments, the location and configuration data 462 may be presented to the instructor I (FIG. 2A) and usable by the instructor I to provide instruction to a remote user. In other embodiments, the location and configuration data 462 may be used to train a model used by a machine learning algorithm for the purposes of automatically providing instruction to a remote user. Still referring to FIG. 4B, the UI data 464 is generally data or information that is stored for the purposes of presenting a user interface to the instructor I (FIG. 2A), data that is generated as a result of use of the user interface, and/or the like. The subject data 466 is generally data or information relating to a subject that is stored for the purposes of providing information to the instructor I (FIG. 2A) and/or a machine learning model and usable to provide accurate instruction to a user, such as a caretaker or the like. For example, the subject data 466 may include electronic medical record (EMR) data, current positioning data, and/or the like. Still referring to FIG. 2B, the other data 468 may generally encompass any other data that may be generated and/or stored for the purposes of providing instruction to a user as described herein.

Included in the non-transitory memory component 454 are the operating logic 454A, the communications logic 454B, and/or the UI logic 454C. The operating logic 454A may include an operating system and/or other software for managing components of the assistive control device 400 and/or remotely operating various components described herein (e.g., the subject care components 140 (FIG. 1), the audiovisual communications components 120 (FIG. 1), and/or the like). The communications logic 454B includes software modules or the like for facilitating communications between the assistive control device 400 and the various components described herein (e.g., the components of the system 100 described in FIG. 1). The UI logic 454C includes software modules or the like for providing the user interface to the instructor I (FIG. 2A) in embodiments where a user interface is provided.

It should be understood that the components illustrated in FIG. 4B are merely illustrative and are not intended to limit the scope of this disclosure. More specifically, while the components in FIG. 4B are illustrated as residing within the assistive control device 400, this is a nonlimiting example. In some embodiments, one or more of the components may reside external to the assistive control device 400. Similarly, as previously described herein, while FIG. 4B is directed to the assistive control device 400, other components such as the data server 490 and/or the one or more machine learning components 470 (FIG. 1) may include similar hardware, software, and/or firmware.

Figure 5:
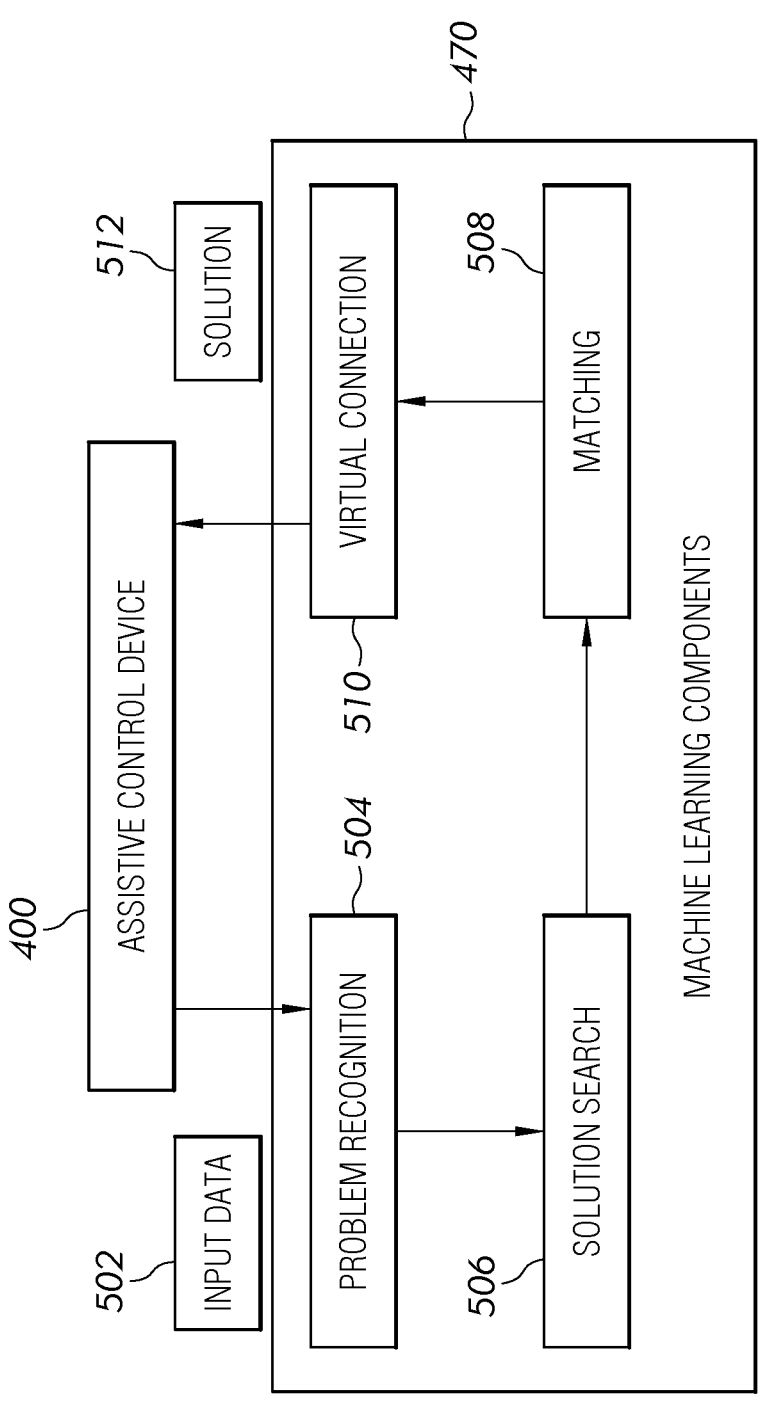
FIG. 5 depicts a flow diagram of an illustrative process completed by a trained machine learning algorithm according to one or more embodiments shown and described herein.
Figure 6:
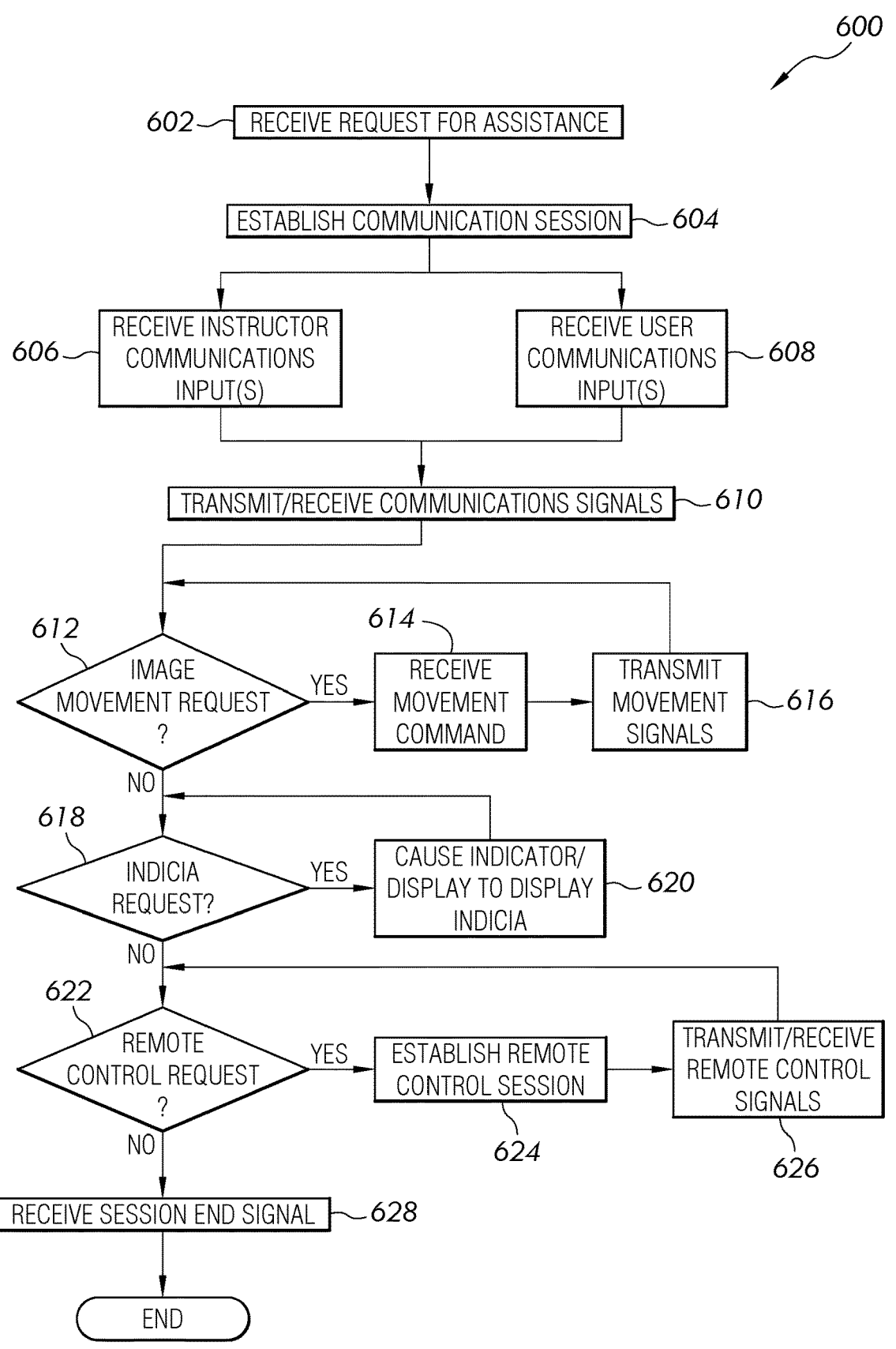
FIG. 6 depicts a flow diagram of an illustrative method of providing a user interface to a user for the purposes of instruction and/or assistance according to one or more embodiments shown and described herein.
Figure 7:
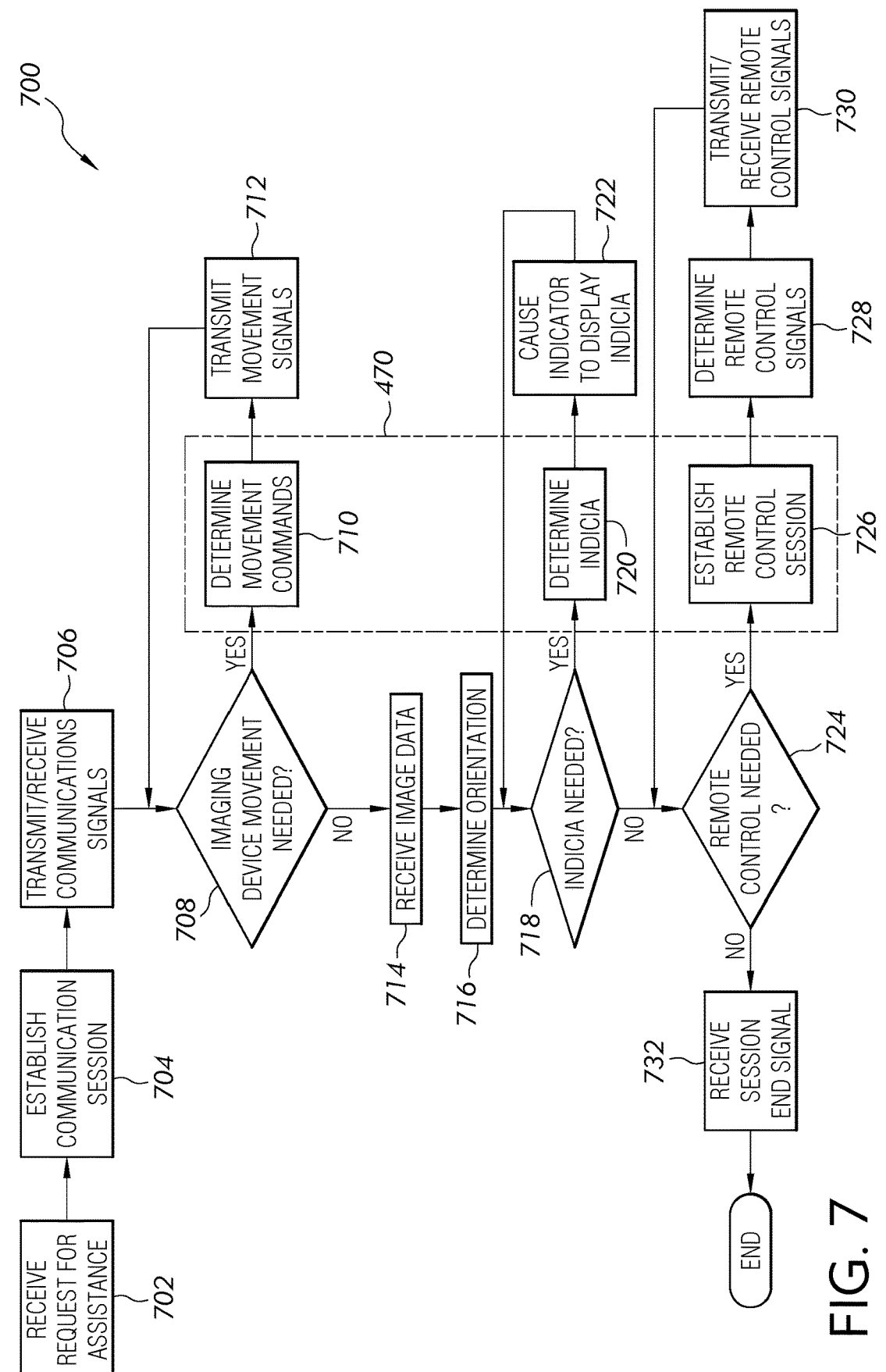
FIG. 7 depicts a flow diagram of an illustrative method of utilizing a trained machine learning algorithm to automatically provide instruction and/or assistance according to one or more embodiments shown and described herein.

The various components that provide the remote instruction and/or remote control capabilities described herein should now be understood. Turning to FIGS. 5-7, various processes for carrying out the remote instruction and/or remote control capabilities will be discussed. FIG. 5 is a flow diagram of an illustrative process completed by a trained machined learning algorithm stored on the one or more machine learning components 470 when data is input (block 502) by the assistive control device 400 according to various embodiments.

At block 504, a problem is recognized. Specifically, the one or more machine learning components 470 can analyze a received unstructured data input (e.g., video, images, audio, text input, and/or the like) such that the unstructured data input can be considered when issuing instructions or completing remote control tasks (e.g., by the assistive control device 400). In some embodiments, the unstructured data may also be used for the purposes of determining whether a user appears to be confused or frustrated, whether certain components are being used in an unsafe or potentially unsafe manner, or the like, as described herein. Once the data is received, the one or more machine learning components 470 analyze the data and utilize the model to recognize the problem.

At block 506, the machine learning components 470 search for a solution and find a particular solution for the particularly identified problem (block 508: "matching"). For example, the machine learning components 470 access a database of previous solutions, determine a previous solution that would solve the identified problem and/or similarities to previous problems and the corresponding solutions thereto. At block 510, the machine learning components develop a solution based on the searching according to block 506 and matching according to block 508 and create a virtual connection between the problem and a devised problem. The solution is then presented at block 512 to the assistive control device 400, which includes a plurality of steps for instructing a user accordingly.

FIG. 6 depicts an illustrative method 600 utilized by the assistive control device 400 (FIG. 1) in embodiments where an instructor I (FIG. 4A) is determining solutions to problems, providing instructions, and/or remote controlling components as described herein. At block 602, the device receives a request for assistance, such as, for example, a signal from a user interface device located in the care space that is actuated by a caretaker, a signal that is generated based on collected data indicating unsafe or potentially unsafe activity, a signal that is generated based on collected data indicating a confused and/or frustrated user, and/or the like.

At block 604, a communications session is established as a result of the request, whereby a communications channel between one or more of the devices and systems described herein is opened. In some embodiments, the communications session may be established automatically or may be presented as a prompt to a user of the assistive control device 400 (FIG. 1), whereby the user is provided with an ability to accept or decline a request to establish a communications session. At blocks 606 and 608, communications inputs are received from the instructor and/or a user and are transmitted at block 610 over the communications channels.

At block 612, a decision is made as to whether an image movement request has been received. That is, if the instructor needs a different view of the care space and provides an input relating thereto, the decision may be "YES" at block 612 and may proceed to block 614. If no input is provided ("NO" at block 612), the process may proceed to block 618. At block 614, one or more movement commands may be received (e.g., via a user interface or the like). As a result, one or more movement signals are transmitted to the camera to cause the camera to move at block 616. The process then reverts to block 612 for any additional movement that may be needed.

At block 618, a determination is made as to whether an indicia request has been received. That is, if the instructor desires to transmit an indicia to a particular area in the care space and provides an input corresponding thereto, the decision may be "YES" at block 618 and may proceed to block 620. If no input is provided ("NO" at block 618), the process may proceed to block 622. At block 620, the type of indicia and location thereof is determined from the inputs and the indicator and/or a remote display are instructed to display the indicia accordingly. The process may proceed back to block 618 and may repeat as necessary for subsequent indicia.

At block 622, a determination is made as to whether a remote control request has been received. That is, if the instructor desires to remotely control one or more components and provides an input corresponding thereto, the decision may be "YES" at block 622 and may proceed to block 624. If no input is provided ("NO" at block 622), the process may proceed to block 628. At block 624, a remote control session may be established by ceding control of a device to the assistive control device. At block 626, as inputs are received at the assistive control device, they are translated into control signals and provided to the device(s) being remotely controlled. The process may proceed back to block 622 and may repeat as necessary for subsequent signals.

At block 628, a session end signal may be received. This may be received from the instructor via the user interface of the assistive control device, from a user in the care space, as a result of a time out process, and/or the like. When such a signal is received, the process may end.

FIG. 7 depicts an illustrative method 700 utilized by the assistive control device 400 (FIG. 1) in embodiments where a machine learning algorithm determines solutions to problems, provides instructions, and/or remote controls components as described herein. At block 702, the device receives a request for assistance, such as, for example, a signal from a user interface device located in the care space that is actuated by a caretaker, a signal that is generated based on collected data indicating unsafe or potentially unsafe activity, a signal that is generated based on collected data indicating a confused and/or frustrated user, and/or the like.

At block 704, a communications session is established as a result of the request, whereby a communications channel between one or more of the devices and systems described herein is opened. Communications signals are transmitted and/or received at block 706 over the communications channels.

At block 708, a decision is made as to whether an image movement request has been received. That is, if a decision is made for a different view of the care space and an input relating thereto is provided, the decision may be "YES" at block 708 and may proceed to block 710 (which is completed by the one or more machine learning components 470, indicated by the dashed line box). If no input is provided ("NO" at block 708), the process may proceed to block 714. At block 710, one or more movement commands are determined. As a result, one or more movement signals are transmitted to the camera to cause the camera to move at block 712. The process then reverts to block 708 for any additional movement that may be needed.

At block 714, image data is received and at block 716, the orientation of items in the care space is determined in order to ensure appropriate instruction and/or remote control is completed. At block 718, a determination is made as to whether indicia is needed. That is, if the machine learning algorithm provides an instruction to transmit an indicia to a particular area in the care space, the decision may be "YES" at block 718 and may proceed to block 720. If no input is provided ("NO" at block 718), the process may proceed to block 724. At block 720, the type of indicia and location thereof is determined and the indicator and/or a remote display are instructed to display the indicia accordingly at block 722. The process may proceed back to block 718 and may repeat as necessary for subsequent indicia.

At block 724, a determination is made as to whether a remote control request has been received. That is, if the machine algorithm determines to remotely control one or more components and provides an input corresponding thereto, the decision may be "YES" at block 724 and may proceed to block 726. If no input is provided ("NO" at block 724), the process may proceed to block 732. At block 726, a remote control session may be established by ceding control of a device to the assistive control device. At block 728, the machine learning algorithm determines remote control signals, and as inputs are received at the assistive control device, they are translated into control signals and provided to the device(s) being remotely controlled t block 730. The process may proceed back to block 724 and may repeat as necessary for subsequent signals.

At block 732, a session end signal may be received. This may be received from the instructor via the user interface of the assistive control device, from a user in the care space, as a result of a time out process, and/or the like. When such a signal is received, the process may end.

Figure 11:
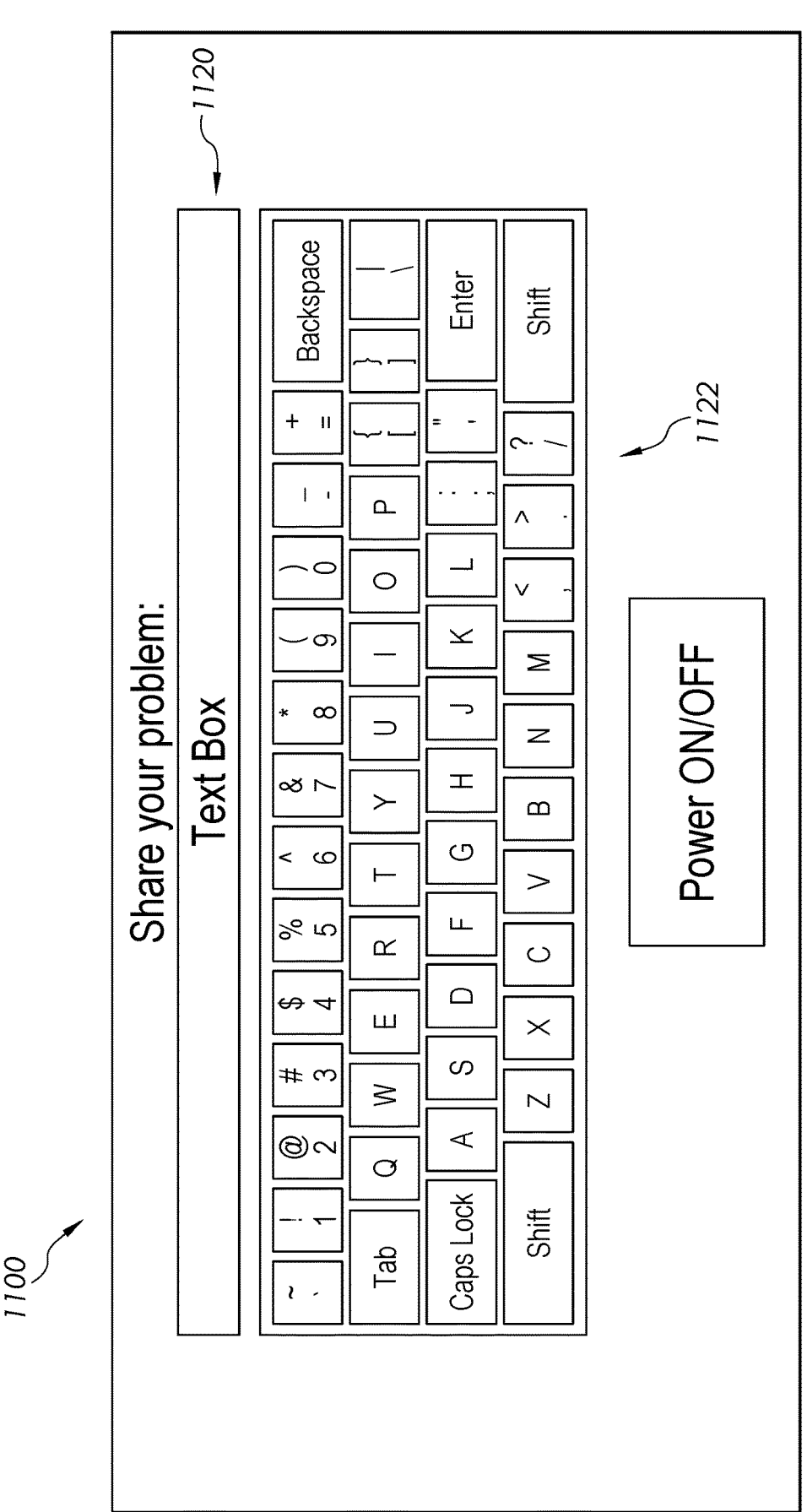
FIG. 11 schematically depicts an illustrative user interface for connecting to a specialist that shows a keyboard and screen according to one or more embodiments shown or described herein.

FIGS. 8-11 depict various user interfaces that may be present on various components described herein and may be used by a user to input a predetermined problem (FIG. 8), select a predetermined solution to the problem (FIG. 9), establish a remote assistance session (FIG. 10), and/or provide text inputs relating to the problem (FIG. 11).

FIG. 8 depicts an illustrative user interface 800 that may be presented, for example, via one or more of the control panels 248, 250, 252 of the subject support apparatus 200 (FIG. 2A), the display 324 of the hand control unit 320 (FIG. 3), the display 382 of the dedicated device controller 380' (FIG. 3), the user interface controls 394 of the wall control unit 390 (FIG. 3), the assistive control device 400 (FIG. 4A), and/or the like. In some embodiments, the user interface 800 may include a header 802 indicative of a particular menu that is being displayed. For example, in the embodiment of FIG. 8, the header 802 may indicate an issue selection menu by displaying text such as, for example, "What's the problem?" Other text, icons, images, and/or the like may also be used to indicate a particular menu that is being displayed. In some embodiments, the user interface 800 may include one or more selectable components 804 that a user can use, for example, to indicate a particular issue. The one or more selectable components 804 may be, for example, preprogrammed selectable buttons that relate to common issues, buttons that are generated and provided on the fly based on particular issues observed occurring in the care space CS (e.g., FIG. 2A), buttons that are generated and provided based on various component settings, or the like. It should be appreciated that the selectable components 804 can be selected by pressing the interface in a location corresponding to a desired location, pressing a keypad button, voicing an input, or the like. Also depicted in the user interface 800 of FIG. 8 is a power button 806 that may be selected, for example, to actuate or deactivate the assistive programming as described herein. For example, if a user does not desire to receive remote input and/or instruction, the user may select the power button 806 to turn off the menu. Similarly, if a user desires remote control and/or instruction as described herein and the user interface 800 is deactivated, pressing the power button 806 may actuate one or menu, turn on one or more components, and/or the like such that remote control and/or instruction can be provided as described herein.

FIG. 9 depicts an illustrative user interface 900 that may be presented, for example, via one or more of the control panels 248, 250, 252 of the subject support apparatus 200 (FIG. 2A), the display 324 of the hand control unit 320 (FIG. 3), the display 382 of the dedicated device controller 380' (FIG. 3), the user interface controls 394 of the wall control unit 390 (FIG. 3), the assistive control device 400 (FIG. 4A), and/or the like. In some embodiments, the user interface 900 may include a header 902 indicative of a particular menu that is being displayed. For example, in the embodiment of FIG. 9, the header 902 may indicate a solution selection menu by displaying text such as, for example, "Select Solution." Other text, icons, images, and/or the like may also be used to indicate a particular menu that is being displayed. In some embodiments, the user interface 900 may include one or more selectable components 904 that a user can use, for example, to select a particular solution to be provided (e.g., via a display, via an augmented reality projection, via one or more indicators, and/or the like, as described herein). The one or more selectable components 904 may be, for example, preprogrammed selectable buttons that relate to common solutions for a particular issue, buttons that are generated and provided on the fly based on particular solutions to particular issues observed occurring in the care space CS (e.g., FIG. 2A), buttons that are generated and provided based on various component settings, or the like. It should be appreciated that the selectable components 904 can be selected by pressing the interface in a location corresponding to a desired location, pressing a keypad button, voicing an input, or the like. Also depicted in the user interface 900 of FIG. 9 is a power button 906 that may function in a manner similar to that of the power button 806 described with respect to FIG. 8. Still referring to FIG. 9, also presented in the user interface 900 is a help button 908, which may function in some ways similar to that of the power button 906. That is, in some embodiments, the help button 908 may be displayed and/or actuated in situations where remote control and/or instruction is requested. For example, in embodiments where pre-programmed tutorials presented as part of the one or more selectable components 904 are not useful or otherwise unhelpful to a user, a user may select the help button 908 to initiate a remote control and/or instruction session as described herein.

FIG. 10 depicts an illustrative user interface 1000 that may be presented, for example, via one or more of the control panels 248, 250, 252 of the subject support apparatus 200 (FIG. 2A), the display 324 of the hand control unit 320 (FIG. 3), the display 382 of the dedicated device controller 380' (FIG. 3), the user interface controls 394 of the wall control unit 390 (FIG. 3), the assistive control device 400 (FIG. 4A), and/or the like. In some embodiments, the user interface 1000 may include a header 1002 indicative of a particular menu that is being displayed. For example, in the embodiment of FIG. 10, the header 1002 may indicate problem input menu by displaying text such as, for example, "Share your problem" Other text, icons, images, and/or the like may also be used to indicate a particular menu that is being displayed. In some embodiments, the user interface 1000 may include one or more selectable components such as, for example, a camera actuation button 1012, a microphone actuation button 1014, a chat button 1016, or the like that a user can use, for example, to particularly select what is and is not shared with a remote user using the assistive control device 400 (FIG. 4A) and/or to actuate a text-based chat instead of a voice-based communication. In some embodiments, the user interface 1000 may also display a video feed preview 1010 which may allow the user of the user interface 1000 to see what video is being transmitted out of the care space (e.g., to the assistive control device 400 (FIG. 4A)). Also depicted in the user interface 1000 of FIG. 10 is a power button 1006 that may function in a manner similar to that of the power button 806 described with respect to FIG. 8.

FIG. 11 depicts an illustrative user interface 1100 that may be displayed when a user actuates a text-based chat by selecting the chat button 1016 depicted in FIG. 10. Specifically, the user interface 1100 includes a text box 1120 that displays text that is transmitted and/or sent, and 1122 depicts a graphical keyboard 1122 that is selectable by the user to enter words, numbers, or the like.

It should now be understood that the systems and methods described herein include a plurality of interconnected devices and systems that provide functionality for allowing a caregiver to use various devices and systems to provide care to a subject and receive remote assistance and/or training that is specific to the devices and systems used and/or according to the subject's particular needs. The remote assistance may be in the form of indicia that show the caregiver how to use equipment, audible instructions, visual instructions, a communications session with a device expert that can interact with the caregiver in real time, remote control of certain devices and systems so that the device expert can show the caregiver what to do or assist the caregiver, and/or the like.

Further aspects of the present disclosure are provided by the subject matter of the following clauses:

A system, comprising: an assistive control device; audio-visual communications components communicatively coupled to the assistive control device, the audiovisual communications components controllable via the assistive control device to selectively capture image and audio within at least a portion of the care space and transmit audio to the care space; and one or more subject care components communicatively coupled to the assistive control device, the one or more subject care components operable locally and remotely via the assistive control device, wherein, upon initiation of a remote assistance session, the audiovisual communications components are operated via the assistive control device to move and capture images of a particular area of concern within the care space, provide two-way communications between the care space and the assistive control device, and provide indicia within the care space, and the one or more subject care components are operated remotely and/or locally to complete one or more care tasks.

The system according any previous clause, further comprising a remote assistance interface device located within the care space that, when actuated, causes initiation of the remote assistance session.

The system according to any previous clause, wherein the remote assistance interface is a help button integrated with at least one of the one or more subject care components.

The system according to any previous clause, wherein the audiovisual communications components comprise at least one omnidirectional camera.

The system according to any previous clause, wherein the at least one omnidirectional camera is integrated with one of the one or more subject care components.

The system according to any previous clause, wherein the audiovisual communications components comprise at least one microphone.

The system according to any previous clause, wherein the at least one microphone is integrated with one of the one or more subject care components.

The system according to any previous clause, wherein the audiovisual communications components comprise a display configured to display at least one of the indicia, a diagram, a set of instructions, a video, an image of a procedure, and an augmented reality projection.

The system according to any previous clause, further comprising an indicator device located within care space, the indicator device comprising a light emitting component that projects the indicia onto at least one of the one or more subject care components and/or a subject.

The system according to any previous clause, wherein the indicia comprises at least one of an arrow, a diagram, one or more words, and a stop signal.

The system according to any previous clause, wherein the assistive control device comprises a trained machine learning algorithm that is configured to automatically receive information pertaining to the care space and the one or more subject care components, and provide instructions for operating the one or more subject care components and/or remotely control the one or more subject care components.

The system according to any previous clause, wherein the assistive control device is configured to determine an orientation of the subject care components within the care space and provide the instructions according to the orientation.

The system according to any previous clause, wherein the assistive control device is configured to direct an indicator device located within the care space to project the indicia onto a body of a subject.

The system according to any previous clause, wherein the assistive control device comprises a display, one or more user interface components, and communications components.

The system according to any previous clause, wherein each of the one or more subject care components is selected from a wall control unit, a dedicated device controller, a mobile lift, a subject support surface, a subject mobility system, a subject monitoring system, and electronically controlled medical equipment.

An assistive control device, comprising: a processor; and a non-transitory, processor-readable medium comprising programming instructions thereon that, when executed, cause the processor to: establish a communication session with one or more remote audiovisual communications components remotely located in a care space in response to a request for assistance, transmit communications signals to and receive communications signals from the one or more remote audiovisual communications components, cause one or more indicator devices to display indicia within the care space, and direct operation of one or more subject care components within the care space.

The assistive control device according to any previous clause, wherein the programming instructions further cause the processor to establish the communication session upon receipt of a request signal from a remote assistance interface device located within the care space.

The assistive control device according to any previous clause, wherein the programming instructions further cause the processor to transmit instructions for repositioning a focus of a camera located within the care space.

The assistive control device according to any previous clause, wherein the programming instructions that cause the one or more indicator devices to display the indicia further cause the one or more indicator devices to emit light that projects the indicia onto at least one of the one or more subject care components and/or a subject.

The assistive control device according to any previous clause, wherein the indicia comprises at least one of an arrow, a diagram, one or more words, and a stop signal.

The assistive control device according to any previous clause, further comprising a storage component storing a trained machine learning algorithm that is configured to automatically receive information pertaining to the care space and the one or more subject care components, and generate programming instructions that cause the processor to provide signals for operating the one or more subject care components and/or remotely control the one or more subject care components.

The assistive control device according to any previous clause, wherein the programming instructions further cause the processor to receive image data of the care space, determine an orientation of the subject care components within the care space, and provide the signals for operating the one or more subject care components based on the orientation.

The assistive control device according to any previous clause, further comprising a display, one or more user interface components, and communications components that allow for a user operating the assistive control device to provide signals for operating the one or more subject care components and/or remotely control the one or more subject care components.

A provider assistance system, comprising: audiovisual communications components coupled to a remote assistive control device, the audiovisual communications components controllable via the assistive control device to selectively capture image and audio within at least a portion of the care space and transmit audio to the care space; one or more subject care components communicatively coupled to the assistive control device, the one or more subject care components operable locally and remotely via the assistive control device; and one or more indicator devices comprising a light emitting component that projects indicia onto at least one of the one or more subject care components and/or a subject, the one or more indicator devices communicatively coupled to the assistive control device.

The provider assistance system according to any previous clause, further comprising a remote assistance interface device that, when actuated causes initiation of a remote assistance session that causes communications between the audiovisual communications and the assistive control device, and initiates a control session between the assistive control device and the one or more subject care components and the one or more indicator devices.

The provider assistance system according to any previous clause, wherein the remote assistance interface is a help button integrated with at least one of the one or more subject care components.

The provider assistance system according to any previous clause, wherein the audiovisual communications components comprise at least one omnidirectional camera.

The provider assistance system according to any previous clause, wherein the at least one omnidirectional camera is integrated with one of the one or more subject care components.

The provider assistance system according to any previous clause, wherein the audiovisual communications components comprise at least one microphone.

The provider assistance system according to any previous clause, wherein the at least one microphone is integrated with one of the one or more subject care components.

The provider assistance system according to any previous clause, wherein the audiovisual communications components comprise a display configured to display at least one of the indicia, a diagram, a set of instructions, a video, an image of a procedure, and an augmented reality projection.

The provider assistance system according to any previous clause, wherein the indicia comprises at least one of an arrow, a diagram, one or more words, and a stop signal.

A method of providing assistance, the method comprising: receiving, at an assistive control device, a request for assistance; establishing a communication session between the assistive control device and one or more remote audiovisual communications components remotely located from the assistive control device in a care space; transmitting communications signals to and receiving communications signals from the one or more remote audiovisual communications components; causing one or more indicator devices to display indicia within the care space; and directing operation of one or more subject care components within the care space.

The method according to any previous clause, further comprising transmitting instructions for repositioning a focus of a camera located within the care space.

The method according to any previous clause, wherein causing the one or more indicator devices to display the indicia further comprises causing the one or more indicator devices to emit light that projects the indicia onto at least one of the one or more subject care components and/or a subject.

The method according to any previous clause, wherein the indicia comprises at least one of an arrow, a diagram, one or more words, and a stop signal.

The method according to any previous clause, further comprising utilizing a trained machine learning algorithm to automatically receive information pertaining to the care space and the one or more subject care components, and operate the one or more subject care components and/or remotely control the one or more subject care components.

The method according to any previous clause, further comprising: receiving image data of the care space; determining an orientation of the subject care components within the care space; and providing the signals for operating the one or more subject care components based on the orientation.

The method according to any previous clause, further comprising: providing, via a user interface of the assistive control device, an indicator corresponding to the request for assistance; and receiving, via the user interface, one or more inputs corresponding to a request to begin an assistance session.

The method according to any previous clause, further comprising: receiving one or more inputs via the user interface, the one or more inputs selected from a camera movement command, a camera zoom command, a microphone actuation command, a microphone deactivation command, and an operation command of the one or more remotely operable devices; and directing operation of the remote subject care components according to the one or more inputs, wherein the remote subject care components provide feedback to a user of the assistive control device and provide for communications between the user of the assistive control device and one or more individuals located at the remote subject care components.

The method according to any previous clause, further comprising: directing a display located near the remote subject care components to display at least one of a diagram, a set of instructions, a video, and an image of a procedure in response to receiving one or more instructions at the user interface of the assistive control device.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A system, comprising:
a machine learning component;
an assistive control device communicatively coupled to the machine learning component;
audiovisual communications components communicatively coupled to the assistive control device, the audiovisual communications components controllable via the assistive control device to selectively capture images and audio within at least a portion of a care space and transmit audio to the care space; and
one or more subject care components comprising one or more person support apparatuses, wherein the one or more subject care components are communicatively coupled to the assistive control device, the one or more subject care components operable locally and remotely via the assistive control device,
wherein, upon initiation of a remote assistance session by a user of the one or more subject care components, the audiovisual communications components are operated via the assistive control device to move and capture images of a particular area of concern within the care space and provide the images to the machine learning component, provide two-way communications between the care space and the assistive control device, and provide indicia within the care space,
wherein the machine learning component is configured to identify an issue related to operation of the one or more subject care components based on the images and/or the audio, and provide at least one potential solution to address the issue, wherein the machine learning component provides the at least one potential solution to address the issue by searching a database for previous solutions corresponding to the identified issue, the at least one potential solution including one or more of the two-way communications, the indicia, or operation of the one or more subject care components, and
wherein the one or more subject care components are operated remotely and/or locally, via selection of a selectable component of the assistive control device to complete one or more care tasks in accordance with the at least one potential solution.

2. The system according to claim 1, further comprising a remote assistance interface device located within the care space that, when actuated, causes initiation of the remote assistance session.

3. The system according to claim 2, wherein the remote assistance interface device is a help button integrated with at least one of the one or more subject care components.

4. The system according to claim 1, wherein the audiovisual communications components comprise:
at least one omnidirectional camera, wherein the at least one omnidirectional camera is integrated with one of the one or more subject care components;
at least one microphone integrated with one of the one or more subject care components; and
a display configured to display at least one of the indicia, a diagram, a set of instructions, a video, an image of a procedure, and an augmented reality projection.

5. The system according to claim 1, further comprising an indicator device located within care space, the indicator device comprising a light emitting component that projects the indicia onto at least one of the one or more subject care components and/or a subject, wherein the indicia comprises at least one of an arrow, a diagram, one or more words, and a stop signal.

6. The system according to claim 1, wherein:

the machine learning component is further configured to determine an orientation of the one or more subject care components within the care space; and the one or more subject care components are operated remotely and/or locally according to the orientation.

7. The system according to claim 1, wherein the assistive control device comprises a display, one or more user interface components, and communications components.

8. The system according to claim 1, wherein each of the one or more subject care components is selected from a wall control unit, a dedicated device controller, a mobile lift, a subject support surface, a subject mobility system, a subject monitoring system, and electronically controlled medical equipment.

9. A provider assistance system, comprising:

a machine learning component;

an assistive control device communicatively coupled to the machine learning component;

an audiovisual communications component coupled to the assistive control device, the audiovisual communications component controllable via the assistive control device to selectively capture an image and audio within at least a portion of a care space and transmit audio to the care space;

a subject care component comprising a person support apparatus, wherein the subject care component is communicatively coupled to the assistive control device, the subject care component operable locally and remotely via the assistive control device, the subject care component selected from a person support apparatus, an overhead lift, a device controller, or a wall control unit; and one or more indicator devices comprising a light emitting component that projects indicia onto at least one of the one or more subject care components and/or a subject, the one or more indicator devices communicatively coupled to the assistive control device, wherein the machine learning component is configured to:

identify an issue related to operation of the subject care component based on the image and the audio, and determine a solution to address the issue, wherein the machine learning component provides the solution to address the issue by searching a database for previous solutions corresponding to the identified issue, and wherein the one or more indicator devices project the indicia in accordance with the solution.

10. The provider assistance system according to claim 9, further comprising a remote assistance interface device that, when actuated causes initiation of a remote assistance session that causes communications between the audiovisual communications component and the assistive control device, and initiates a control session between the assistive control device and the subject care component and the one or more indicator devices, wherein the remote assistance interface device is a help button integrated with at least one of the one or more subject care components.

11. The provider assistance system according to claim 9, wherein the audiovisual communications component comprises:

at least one omnidirectional camera, wherein the at least one omnidirectional camera is integrated with the subject care component;

at least one microphone, wherein the at least one microphone is integrated with the subject care component; and a display configured to display at least one of the indicia, a diagram, a set of instructions, a video, an image of a procedure, and an augmented reality projection.

12. The provider assistance system according to claim 9, wherein the indicia comprises at least one of an arrow, a diagram, one or more words, and a stop signal.

13. A method of providing assistance, the method comprising:

receiving, at an assistive control device, a request for assistance in operating a subject care component, wherein the subject care component comprises a person support apparatus;

capturing an image and/or audio in a care space comprising the subject care component;

providing the image and/or the audio to a machine learning component configured to process the image and/or the audio to identify an issue related to operation of the subject care component and determine a solution to address the issue, wherein the machine learning component determines the solution to address the issue by searching a database for previous solutions corresponding to the identified issue; and completing at least one of the following in accordance with the solution:

causing one or more indicator devices to display indicia within the care space;

providing two-way communications between an audiovisual communications component in the care space and the assistive control device; or directing operation of the one or more subject care components within the care space.

14. The method according to claim 13, further comprising transmitting instructions for repositioning a focus of a camera located within the care space.

15. The method according to claim 13, wherein causing the one or more indicator devices to display the indicia further comprises causing the one or more indicator devices to emit light that projects the indicia onto at least one of the one or more subject care components and/or a subject.

16. The method according to claim 13, wherein the indicia comprises at least one of an arrow, a diagram, one or more words, and a stop signal.

17. The method according to claim 13, further comprising:

determining an orientation of the one or more subject care components within the care space, wherein directing operation of the one or more subject care components is based on the orientation.

18. The method according to claim 13, further comprising:

providing a user interface; and receiving, via the user interface, one or more inputs corresponding to the request for assistance.

19. The method according to claim 18, further comprising:

receiving one or more inputs via the user interface, the one or more inputs selected from a camera movement command, a camera zoom command, a microphone actuation command, a microphone deactivation command, and an operation command of the subject care component;

directing operation of the subject care component according to the one or more inputs, wherein the subject care component provide feedback to a user of the assistive control device and provide for communications between the user of the assistive control device and one or more individuals located at the subject care component; and directing a display located near the subject care component to display at least one of a diagram, a set of instructions, a video, and an image of a procedure in response to receiving one or more instructions at the user interface of the assistive control device.

20. The system according to claim 1, wherein:

the care space is a virtual care space used for training users of the assistive control device; and the one or more subject care components comprise a virtual subject care component.

* * * * *